(12) United States Patent
Kamachi et al.

(10) Patent No.: US 7,846,970 B2
(45) Date of Patent: Dec. 7, 2010

(54) HYDROXYCITRIC ACID DERIVATIVES AND SKIN EXTERNAL PREPARATIONS CONTAINING THE SAME

(75) Inventors: Harumi Kamachi, Chiba (JP); Tsuyoshi Katoh, Chiba (JP); Hirobumi Aoki, Chiba (JP)

(73) Assignee: Showa Denko K.K., Tokyo (JP)

( * ) Notice: Subject to any disclaimer, the term of this patent is extended or adjusted under 35 U.S.C. 154(b) by 379 days.

(21) Appl. No.: 11/663,422

(22) PCT Filed: Sep. 22, 2005

(86) PCT No.: PCT/JP2005/018069

§ 371 (c)(1),
(2), (4) Date: Mar. 21, 2007

(87) PCT Pub. No.: WO2006/033476

PCT Pub. Date: Mar. 30, 2006

(65) Prior Publication Data

US 2007/0293577 A1    Dec. 20, 2007

Related U.S. Application Data

(60) Provisional application No. 60/614,327, filed on Sep. 30, 2004, provisional application No. 60/674,692, filed on Apr. 26, 2005.

(30) Foreign Application Priority Data

| Sep. 24, 2004 | (JP) | ............... 2004-276712 |
| Apr. 18, 2005 | (JP) | ............... 2005-119826 |
| Jun. 24, 2005 | (JP) | ............... 2005-185253 |

(51) Int. Cl.
*A01N 37/00* (2006.01)
*C07C 59/245* (2006.01)
*C07C 69/66* (2006.01)

(52) U.S. Cl. ............ 514/574; 562/582; 562/584; 560/182

(58) Field of Classification Search ........ 514/574; 562/584; 560/182
See application file for complete search history.

(56) References Cited

U.S. PATENT DOCUMENTS

| 3,341,419 | A | * | 9/1967 | Rappaport et al. ........ 424/59 |
| 3,764,692 | A | * | 10/1973 | Lowenstein ........... 514/449 |
| 3,810,931 | A | | 5/1974 | Guthrie et al. |
| 3,855,407 | A | * | 12/1974 | Klein ................ 424/59 |
| 3,994,927 | A | | 11/1976 | Guthrie et al. |
| 6,066,311 | A | * | 5/2000 | Cheetham et al. ....... 424/60 |
| 2005/0136014 | A1 | * | 6/2005 | Gonzalez et al. ....... 424/59 |
| 2005/0282894 | A1 | | 12/2005 | Raju |
| 2007/0232698 | A1 | * | 10/2007 | Shibuya et al. ........ 514/561 |

FOREIGN PATENT DOCUMENTS

| FR | 2 716 374 A | 8/1995 |
| FR | 2716374 A1 | 8/1995 |
| FR | 2729856 A1 | 8/1996 |
| JP | 2001527022 A | 12/2001 |
| WO | 9605741 A1 | 2/1996 |
| WO | WO 2005115326 | * 12/2005 |

OTHER PUBLICATIONS

Ozawa, T. et al. Three New Substituted Cinnamoyl Hydroxycitric Acids, 1997, Agric. Biol. Chem., vo. 41, (2), 1997, pp. 359-367.*
Route of Administration, http://en.wikipedia.org/wiki/Route_of_administration, 2009, (5 pages).*
Jena et al., Chemistry and biochemistry of (-)-Hydroxycitric acid from Garcinia, 2002, Journal of Agricultural and Food Chemistry, vol. 50, No. 1, pp. 10-22.*
Tetsuo Ozawa et al., "Three New Substituted Cinnamoyl Hydroxycitric Acids from Corn Plant", Agricultural and Biological Chemistry, Japan Society for Bioscience, Biotechnology and Agrochem., 1977, p. 359-367, vol. 41, No. 2.
J. Corthout et al., "Antiviral Caffeoyl Esters From *Spondias mombin*", Phytochemistry, 1992, pp. 1979-1981, vol. 31, No. 6, Pergamon Press, GB.

* cited by examiner

*Primary Examiner* — Rosalynd Keys
*Assistant Examiner* — Yate' K Cutliff
(74) *Attorney, Agent, or Firm* — Sughrue Mion, PLLC

(57) ABSTRACT

Hydroxycitric acid derivatives and salts thereof are provided which are useful as active ingredients of skin external preparations and cosmetics. Also provided are processes for production of the hydroxycitric acid derivatives, and skin external preparations and cosmetics containing the hydroxycitric acid derivatives. Specific hydroxycitric acid derivatives or salts thereof are produced wherein at least one of the hydroxyl groups of hydroxycitric acid or least one of the hydroxyl groups and at least one carboxyl group of hydroxycitric acid are modified to linkage moieties breakable by biological enzyme reaction. The hydroxycitric acid derivatives or salts thereof are added in skin external preparations and cosmetics.

24 Claims, No Drawings

HYDROXYCITRIC ACID DERIVATIVES AND SKIN EXTERNAL PREPARATIONS CONTAINING THE SAME

CROSS-REFERENCE TO RELATED APPLICATIONS

This application is an application filed under 35 U.S.C.§111(a) claiming benefit pursuant to 35 U.S.C.§119(e) of the filing dates of Provisional Application Nos. 60/614,327 and 60/674,692 filed Sep. 30, 2004 and Apr. 26, 2005, respectively, pursuant to 35 U.S.C.§111(b).

FIELD OF THE INVENTION

The present invention relates to hydroxycitric acid derivatives, processes for production thereof, and skin external preparations containing the derivatives.

More particularly, the invention relates to hydroxycitric acid derivatives having slimming effects, processes for production thereof, and skin external preparations containing the derivatives.

BACKGROUND OF THE INVENTION

The fat in the body is generally considered to be the result of an accumulation of neutral fat within white adipocytes by energy ingestion in excess of metabolism energy.

The accumulation of body fat causes obesity, which is aesthetically unfavorable and leads to various diseases including arteriosclerosis. Such health and cosmetic concerns have created a growing desire for a firm body.

However, the obesity is nowadays increasing for many reasons including overeating, physical inactivity and stress. As such, decreasing the subcutaneous fat and preventing the accumulation thereof are now substantial problems for people irrespective of age. Traditional slimming methods include diet restriction, exercise and ingestion of digestion and absorption inhibiting food, in addition to which external preparations such as cosmetics for topical slimming have been increasingly used.

Specifically, cosmetics such as skin milks, creams, skin toners, packs and cleansing preparations, and external preparations such as ointments, dispersion liquids, cream agents and external liquid agents are mixed with medicinal ingredients for slimming effects. Such medicinal ingredients include caffeine, hedera rhombea extracts, hamamelis extracts, green tea extracts, tea extracts, oolong tea extracts and seaweed extracts.

Many of the medicinal ingredients have a purpose of facilitating breakdown of accumulated fat. Slimming external preparations that contain garcinia cambogia extracts for inhibiting fat synthesis have more recently attracted attention, as described in Patent Documents 1 and 2.

The garcinia cambogia extracts are known to contain much hydroxycitric acid, and the use of concentrated extract thereof in foods and the like is described in, for example, Patent Document 3.

Further, Patent Document 4 discloses the use of hydroxycitric acid in the form of calcium or sodium salt for increasing water solubility and stability of hydroxycitric acid.

However, traditional external preparations containing hydroxycitric acid and/or salts thereof (hereinafter, hydroxycitric acids) have been unable to produce satisfactory effects.

The hydroxycitric acid is usually used as calcium salt that is stable, but in such cases the feeling of use particularly as external preparations is very bad and has been desired to improve.

[Patent Document 1] French Patent Publication Bulletin No. 2716374
[Patent Document 2] French Patent Publication Bulletin No. 2729856
[Patent Document 3] WO 96/05741
[Patent Document 4] JP-A-2001-527022

DISCLOSURE OF THE INVENTION

One of the reasons for the conventional external preparations with the hydroxycitric acids producing unsatisfactory effects is probably that the hydroxycitric acids have very high water solubility and therefore their direct use results in poor skin affinity and percutaneous absorption properties, making it difficult for enough hydroxycitric acids to permeate to a tissue in which the fat metabolism is to be performed.

Addition of the hydroxycitric acids in large amounts in order to achieve good effects probably worsens the feeling of use as external preparation and deteriorates the stability of formulations such that they change odors and colors.

It is an object of the invention to provide novel hydroxycitric acid derivatives and salts thereof capable of solving the problems of traditional hydroxycitric acids.

It is another object of the invention to provide processes for production of the novel hydroxycitric acid derivatives and salts thereof.

It is a further object of the invention to provide skin external preparations and cosmetics containing the novel hydroxycitric acid derivatives and/or salts thereof.

It is a still further object of the invention to provide skin external preparations and cosmetics containing hydroxycitric acid derivatives from natural extracts and/or salts thereof.

The present inventors made extensive and intensive studies in order to solve the aforementioned problems and have found that hydroxycitric acid derivatives and salts thereof in which at least one of the hydroxyl groups at the 2-position and the 3-position of hydroxycitric acid is modified are effective for solving the above problems. The present invention has been completed based on the finding.

Specifically, the present invention concerns the following [1] to [14].

[1] A hydroxycitric acid derivative represented by the formula (I) below or salt thereof:

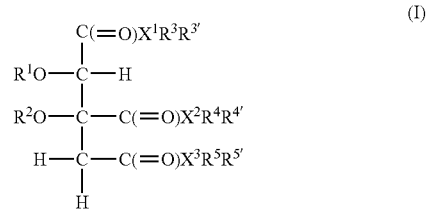

wherein $R^1$ and $R^2$ are each a hydrogen atom or a group removable by biological enzyme reaction (with the proviso that $R^1$ and $R^2$ cannot be hydrogen atoms at the same time), the removable group being selected from those represented by the formula (Ia) below; $X^1$ to $X^3$ are each a nitrogen atom or an oxygen atom; and $R^3$, $R^4$, $R^5$, $R^{3'}$, $R^{4'}$ and $R^{5'}$ are each a hydrogen atom or a chain hydrocarbon group of 1 to 30 carbon atoms that may have a branch or an unsaturated bond (with the proviso that when any of $X^1$, $X^2$ and $X^3$ is an oxygen atom, corresponding $R^{3'}$, $R^{4'}$ or $R^{5'}$ does not exist);

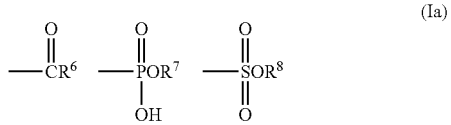

wherein $R^6$ to $R^8$ are each a hydrogen atom, an aryl group, or a chain hydrocarbon group of 1 to 30 carbon atoms that may have a branch, an unsaturated bond or a substituent group.

[2] The hydroxycitric acid derivative or salt thereof as described in [1], wherein in the formula (Ia), $R^6$ is a chain hydrocarbon group of 7 to 23 carbon atoms that may have a branch, an unsaturated bond or a substituent group, and $R^7$ and $R^8$ are each a hydrogen atom or a chain hydrocarbon group of 8 to 24 carbon atoms that may have a branch, an unsaturated bond or a substituent group.

[3] The hydroxycitric acid derivative or salt thereof as described in [1], wherein in the formula (I), $R^3$ to $R^5$ are each a hydrogen atom or a chain hydrocarbon group of 1 to 30 carbon atoms that may have a branch or an unsaturated bond, and $X^1$ to $X^3$ are all oxygen atoms; and wherein in the formula (Ia), $R^6$ is a chain hydrocarbon group of 7 to 23 carbon atoms that may have a branch, an unsaturated bond or a substituent group, and $R^7$ and $R^8$ are each a hydrogen atom or a chain hydrocarbon group of 8 to 24 carbon atoms that may have a branch, an unsaturated bond or a substituent group.

[4] The hydroxycitric acid derivative or salt thereof as described in [1], wherein in the formula (I), $R^2$ is a hydrogen atom, $R^3$ to $R^5$ are all hydrogen atoms, and $X^1$ to $X^3$ are all oxygen atoms; and wherein in the formula (Ia), $R^6$ is a chain hydrocarbon group of 13 to 21 carbon atoms that may have a branch, an unsaturated bond or a substituent group.

[5] The hydroxycitric acid derivative or salt thereof as described in [1], wherein in the formula (I), $R^2$ is a hydrogen atom, $R^3$ to $R^5$ are each a hydrogen atom or a chain hydrocarbon group of 1 to 30 carbon atoms that may have a branch or an unsaturated bond (with the proviso that $R^3$ to $R^5$ cannot be hydrogen atoms at the same time), and $X^1$ to $X^3$ are all oxygen atoms; and wherein in the formula (Ia), $R^6$ is a chain hydrocarbon group of 13 to 21 carbon atoms that may have a branch, an unsaturated bond or a substituent group.

[6] A process for producing the hydroxycitric acid derivative or salt thereof as described in any one of [1] to [5], which process comprises reacting hydroxycitric acid and/or an alkali metal salt thereof and/or an alkaline earth metal salt thereof, with a carboxylic acid derivative, a phosphoric acid derivative or a sulfonic acid derivative that is capable of in vivo cleavage, in a solvent.

[7] A process for producing the hydroxycitric acid derivative or salt thereof as described in [4] or [5], which process comprises:

a first step comprising reacting hydroxycitric acid and/or an alkali metal salt thereof and/or an alkaline earth metal salt thereof, with an alcohol in a solvent to prepare a hydroxycitric acid (tri)ester;

a second step comprising reacting the compound obtained in the first step with an aliphatic carboxylic acid derivative capable of in vivo cleavage to esterify a hydroxyl group of the compound obtained in the first step; and a third step comprising cleaving ester linkage moieties of the compound obtained in the second step so as to cleave part or all of the ester linkage moieties formed in the first step.

[8] A skin external preparation comprising the hydroxycitric acid derivative and/or salt thereof as described in any one of [1] to [5].

[9] The skin external preparation as described in [8], wherein the preparation contains the hydroxycitric acid derivative and/or salt thereof in an amount of 0.01 to 20% by mass.

[10] The skin external preparation as described in [8] or [9], wherein the preparation further contains a substance capable of increasing hormone-sensitive lipase activity.

[11] The skin external preparation as described in any one of [8] to [10], wherein the preparation further contains a substance capable of facilitating breakdown of fatty acids.

[12] A skin external preparation comprising a hydroxycitric acid derivative of the formula (III) below and/or a salt thereof:

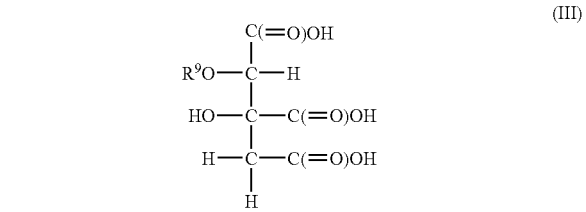

wherein $R^9$ is an acyl group comprising a cinnamic acid residue, a caffeic acid (caffeine acid) residue or a chlorogenic acid residue.

[13] A cosmetic comprising the skin external preparation as described in any one of [8] to [11].

[14] A cosmetic comprising the skin external preparation as described in [12].

The hydroxycitric acid derivatives or salts thereof according to the present invention have high skin affinity and/or percutaneous absorption properties, and are broken down to hydroxycitric acid by biological enzyme reaction after absorbed in a body. Therefore, the hydroxycitric acid derivatives or salts thereof according to the present invention can increase the absorption efficiency of hydroxycitric acid in the body and enable tissues where fat is synthesized to receive enough hydroxycitric acid.

The present invention uses the hydroxycitric acid derivatives and/or salts thereof as ingredients in skin external preparations that are expected to inhibit fat synthesis in tissues where fat is synthesized, and thereby the invention provides skin external preparations that are effective, possess good feeling of use, and are highly stable.

The production processes according to the present invention can efficiently produce the hydroxycitric acid derivatives or salts thereof.

Combined use of the hydroxycitric acid derivatives and/or salts thereof with a substance capable of increasing hormone-sensitive lipase activity or a substance capable of facilitating breakdown of fatty acids leads to skin external preparations that will produce effects of inhibiting the fat synthesis and facilitating the fat breakdown.

PREFERRED EMBODIMENTS OF THE INVENTION

The present invention will be described in detail hereinbelow.

<Hydroxycitric Acid Derivatives and Salts Thereof>

The hydroxycitric acid derivatives of the invention will be discussed.

The hydroxycitric acid derivatives of the invention are compounds represented by the formula (I) below:

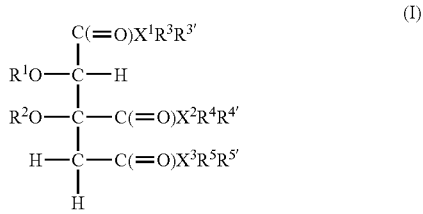

(I)

In the formula (I), $R^1$ and $R^2$ are each a hydrogen atom or a group removable by biological enzyme reaction that is selected from those represented by the formula (Ia) (with the proviso that $R^1$ and $R^2$ cannot be hydrogen atoms at the same time):

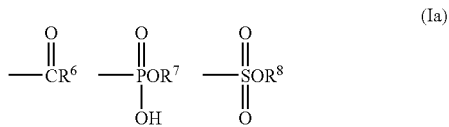

(Ia)

Specifically, at least one of $R^1$ and $R^2$ is preferably a group removable by biological enzyme reaction and represented by any of the formula (Ia). Either or both of $R^1$ and $R^2$ may be such groups. In a preferred embodiment, either $R^1$ or $R^2$ is such a group. In a particularly preferred embodiment, $R^1$ is a group removable by biological enzyme reaction and represented by any of the formula (Ia), and $R^2$ is a hydrogen atom.

In the formula (Ia), $R^6$ to $R^8$ are each a hydrogen atom, an aryl group, or a chain hydrocarbon group of 1 to 30 carbon atoms that may have a branch, an unsaturated bond or a substituent group. As used herein, the groups removable by biological enzyme reaction mean groups that are hydrolyzed by a hydrolase such as esterase present in vivo with the result that $R^1$ and $R^2$ become hydrogen atoms.

The aryl groups include phenyl, naphthyl, furyl, thienyl and pyridyl groups. The chain hydrocarbon groups of 1 to 30 carbon atoms that may have a branch, an unsaturated bond or a substituent group include those that constitute part of the acyl groups described below as $R^1$ and/or $R^2$.

Preferably, $R^6$ to $R^8$ are each a hydrogen atom or a chain hydrocarbon group of 1 to 30 carbon atoms that may have a branch, an unsaturated bond or a substituent group.

Specifically, $R^6$ is a chain hydrocarbon group of 7 to 23 carbon atoms, preferably 13 to 21 carbon atoms that may have a branch, an unsaturated bond or a substituent group, and is more preferably a saturated chain hydrocarbon group of 13 to 21 carbon atoms that may have a branch; $R^7$ and $R^8$ are each a hydrogen atom or a chain hydrocarbon group of 8 to 24 carbon atoms that may have a branch, an unsaturated bond or a substituent group, preferably each a hydrogen atom or such a chain hydrocarbon group of 14 to 22 carbon atoms, and more preferably each a hydrogen atom.

The groups removable by biological enzyme reaction and represented by the formula (Ia) desirably have 8 to 24 carbon atoms, preferably 14 to 22 carbon atoms.

The substituent groups include halogen atoms, and amino, cyano, alkoxy and nitro groups.

Examples of the derivatives in which the hydroxyl group in the molecule is modified include compounds of the formula (I) in which $R^1$ and/or $R^2$ is any of:

hexanoyl, 2-methylpentanoyl, 3-methylpentanoyl, 4-methylpentanoyl, 2-ethylbutanoyl, heptanoyl, 2-methylhexanoyl, 3-methylhexanoyl, 4-methylhexanoyl, 2-ethylpentanoyl, 3-ethylpentanoyl, octanoyl, 2-methylheptanoyl, 3-methylheptanoyl, 4-methylheptanoyl, 5-methylheptanoyl, 6-methylheptanoyl, 2-ethylhexanoyl, 3-ethylhexanoyl, 4-ethylhexanoyl, 2-propylpentanoyl, nonanoyl, decanoyl, undecanoyl, 10-undecenoyl, dodecanoyl, tridecanoyl, tetradecanoyl, pentadecanoyl, hexadecanoyl, 9-hexadecenoyl, heptadecanoyl, octadecanoyl, isostearyl, cis-9-octadecenoyl, 11-octadecenoyl, cis,cis-9,12-octadecadienoyl, 9,12,15-octadecatrienoyl, 6,9,12-octadecatrienoyl, 9,11,13-octadecatrienoyl, nonadecanoyl, 2,6,10,14-tetramethylpentadecanoyl, icosanoyl, 8,11-icosadienoyl, 5,8,11-icosatrienoyl, 5,8,11,14-icosatetraenoyl, 3,7,11,15-tetramethylhexadecanoyl, heneicosanoyl and docosanoyl groups.

Of these, preferred are compounds of the formula (I) in which $R^1$ and/or $R^2$ is any of octanoyl, decanoyl, undecanoyl, dodecanoyl, hexadecanoyl, octadecanoyl and isostearyl groups.

More preferred are compounds in which $R^1$ is any of octanoyl, decanoyl, undecanoyl, dodecanoyl, hexadecanoyl, octadecanoyl and isostearyl groups, and $R^2$ is a hydrogen atom.

In the formula (I), $X^1$ to $X^3$ are each a nitrogen atom or an oxygen atom; and $R^3$, $R^4$, $R^5$, $R^{3'}$, $R^{4'}$ and $R^{5'}$ are each a hydrogen atom or a chain hydrocarbon group of 1 to 30 carbon atoms that may have a branch or an unsaturated bond (with the proviso that when any of $X^1$, $X^2$ and $X^3$ is an oxygen atom, corresponding $R^{3'}$, $R^{4'}$ or $R^{5'}$ does not exist).

When any of $X^1$ to $X^3$ is a nitrogen atom, —CONR$^m$R$^{m'}$ (where m and m' represent identical numbers of any of 3, 4 and 5 corresponding to $X^1$ to $X^3$) is a substituted or unsubstituted amide group breakable by biological enzyme reaction. When any of $X^1$ to $X^3$ is an oxygen atom, —COOR$^m$ (where m represents a number of any of 3, 4 and 5 corresponding to $X^1$ to $X^3$) is a carboxyl group, or an ester group breakable by biological enzyme reaction.

By the substituted or unsubstituted amide group breakable by biological enzyme reaction, it is understood that the substituted or unsubstituted amide group is hydrolyzed into a carboxyl group by a hydrolase such as amidase present in vivo.

By the ester group breakable by biological enzyme reaction, it is understood that the ester group is hydrolyzed into a carboxyl group by a hydrolase such as esterase present in vivo.

With the above proviso, $R^3$, $R^4$, $R^5$, $R^{3'}$, $R^{4'}$ and $R^{5'}$ are each a hydrogen atom or a chain hydrocarbon group of 1 to 30 carbon atoms, preferably 8 to 24 carbon atoms, more preferably 14 to 22 carbon atoms that may have a branch or an unsaturated bond; more preferably, they are each a hydrogen atom or a saturated chain hydrocarbon group of 14 to 22 carbon atoms that may have a branch. These groups may also be saccharide residues derived from monosaccharides and polysaccharides.

Specifically, $R^3$, $R^4$, $R^5$, $R^{3'}$, $R^{4'}$ and $R^{5'}$ are each any of a hydrogen atom, methyl group, ethyl group, propyl group, isopropyl group, butyl group, 1-methylpropyl group, 2-methylpropyl group, pentyl group, 1-methylbutyl group, 2-methylbutyl group, 3-methylbutyl group, 1-ethylpropyl group, hexyl group, 1-methylpentyl group, 2-methylpentyl group, 3-methylpentyl group, 4-methylpentyl group, 1-ethylbutyl group, 2-ethylbutyl group, heptyl group, 1-methylhexyl group, 2-methylhexyl group, 3-methylhexyl group, 4-methylhexyl group, 5-methylhexyl group, 1-ethylpentyl group, 2-ethylpentyl group, 3-ethylpentyl group, octyl group, 1-methylheptyl group, 2-methylheptyl group, 3-methylheptyl group, 4-methylheptyl group, 5-methylheptyl group, 6-methylheptyl group, 1-ethylhexyl group, 2-ethylhexyl group, 3-ethylhexyl group, 4-ethylhexyl group, 1-propylpentyl group, 2-propylpentyl group, nonyl group, decyl group, undecyl group, 10-undecenyl group, dodecyl group, tridecyl group, tetradecyl group, pentadecyl group, hexadecyl group, 9-hexadecenyl group, heptadecyl group, octadecyl group, isostearyl group, cis-9-octadecenyl group, 11-octadecenyl group, cis,cis-9,12-octadecadienyl group, 9,12,15-octadecatrienyl group, 6,9,12-octadecatrienyl group, 9,11,13-octadecatrienyl group, nonadecyl group, 2,6,10,14-tetramethylpentadecyl group, icosanyl group, 8,11-icosadienyl group, 5,8,11-icosatrienyl group, 5,8,11,14-icosatetraenyl group, 3,7,11,15-tetramethylhexadecyl group, heneicosanyl group and docosanyl group.

In a preferred embodiment with the above proviso, $R^3$, $R^4$, $R^5$, $R^{3'}$, $R^{4'}$ and $R^{5'}$ are each any of a hydrogen atom, methyl group, ethyl group, propyl group, isopropyl group, butyl group, hexyl group, octyl group, decyl group, undecyl group, dodecyl group, tridecyl group, tetradecyl group, pentadecyl group, hexadecyl group, heptadecyl group, octadecyl group and isostearyl group.

In a more preferred embodiment, one or two of $R^3$, $R^4$, $R^5$, $R^{3'}$, $R^{4'}$ and $R^{5'}$ are each any of methyl group, ethyl group, propyl group, isopropyl group, butyl group, hexyl group, octyl group, decyl group, undecyl group, dodecyl group, tridecyl group, tetradecyl group, pentadecyl group, hexadecyl group, heptadecyl group, octadecyl group and isostearyl group, and the others are all hydrogen atoms.

$X^1$ to $X^3$ are each a nitrogen atom or an oxygen atom, and may be the same or different from each other. Preferably, they are the same atoms, and more preferably they are oxygen atoms.

When $X^1$ to $X^3$ are all oxygen atoms, the modified carboxyl group moieties are represented by $—COOR^m$ (where m represents a number of any of 3, 4 and 5 depending on $X^1$ to $X^3$) and are carboxyl groups or ester groups breakable by biological enzyme reaction. In this case, $R^{3'}$, $R^{4'}$ and $R^{5'}$ do not exist.

Preferred examples of the hydroxycitric acid derivatives of the invention include compounds occurring by modifying at least one of the hydroxyl groups at the 2-position and the 3-position of hydroxycitric acid, and compounds occurring by modifying at least one carboxyl group in the above compounds.

Examples of the derivatives with modified carboxyl group(s) include compounds corresponding to the aforementioned derivatives with modified hydroxyl group(s), except that at least one carboxyl group is modified to a substituted or unsubstituted amide group breakable by biological enzyme reaction or an ester group breakable by biological enzyme reaction.

That is, the hydroxycitric acid derivatives according to the present invention include compounds in which at least one of the hydroxyl groups is modified and no carboxyl group is modified, and compounds in which at least one of the hydroxyl groups and at least one carboxyl group are modified.

Preferable examples of such compounds include compounds having combined definitions of $R^1$, $R^2$, $X^1$ to $X^3$, $R^3$, $R^4$, $R^5$, $R^{3'}$, $R^{4'}$ and $R^{5'}$.

As described above, the modification may be performed in various combinations of the functional groups in the molecule. Particularly preferred examples include:

compounds of the formula (IIa) below in which $R^2$ is a hydrogen atom, $R^3$ to $R^5$ are all hydrogen atoms, and $X^1$ to $X^3$ are all oxygen atoms; and compounds of the formula (IIb) below in which $R^2$ is a hydrogen atom, $R^3$ to $R^5$ are each a hydrogen atom or a chain hydrocarbon group of 1 to 30 carbon atoms that may have a branch or an unsaturated bond (with the proviso that $R^3$ to $R^5$ cannot be hydrogen atoms at the same time), and $X^1$ to $X^3$ are all oxygen atoms.

In these preferred cases, $R^1$ is any of the groups removable by biological enzyme reaction that are represented by the formula (Ia) above, in which $R^6$ is preferably a chain hydrocarbon group of 13 to 21 carbon atoms that may have a branch, an unsaturated bond or a substituent group. More preferably, $R^1$ is an acyl group of 14 to 22 carbon atoms.

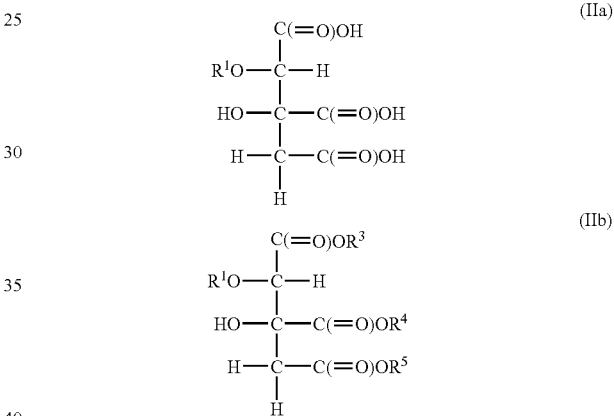

Specific examples of the hydroxycitric acid derivatives of the invention include hydroxycitric acid-2-octanoate, hydroxycitric acid-2-caprate, hydroxycitric acid-2-laurate, hydroxycitric acid-2-myristate, hydroxycitric acid-2-palmitate, hydroxycitric acid-2-stearate, hydroxycitric acid-2-behenate, hydroxycitric acid-2-isopalmitate, hydroxycitric acid-2-isostearate, hydroxycitric acid-2-hexyldecanoate, hydroxycitric acid-2-linoleate, hydroxycitric acid monomoethyl ester-2-myristate, hydroxycitric acid monomethyl ester-2-palmitate and hydroxycitric acid monomethyl ester-2-stearate.

Of these, preferred are hydroxycitric acid-2-laurate, hydroxycitric acid-2-myristate, hydroxycitric acid-2-palmitate, hydroxycitric acid-2-stearate, hydroxycitric acid-2-behenate, hydroxycitric acid-2-isopalmitate, hydroxycitric acid-2-isostearate, hydroxycitric acid-2-hexyldecanoate and hydroxycitric acid-2-linoleate.

More preferred are hydroxycitric acid-2-myristate, hydroxycitric acid-2-palmitate and hydroxycitric acid-2-stearate.

Examples of the salts of the hydroxycitric acid derivatives include alkali metal salts and alkaline earth metal salts of the above hydroxycitric acid derivatives.

The alkali metal salts include sodium salts and potassium salts, and the alkaline earth metal salts include calcium salts.

<Processes for Producing Hydroxycitric Acid Derivatives or Salts Thereof>

The processes for producing the hydroxycitric acid derivatives or salts thereof will now be described.

There is particularly no limitation on the process for producing the hydroxycitric acid derivatives or salts thereof. For example, hydroxycitric acid and/or an alkali metal salt thereof and/or an alkaline earth metal salt thereof may be reacted with a carboxylic acid derivative, a phosphoric acid derivative or a sulfonic acid derivative that is capable of in vivo cleavage, in an appropriate solvent.

Exemplary processes involving commercially available hydroxycitric acid as starting material include:

(1) The hydroxyl group(s) of hydroxycitric acid is directly esterified;

(2) The carboxyl group(s) of hydroxycitric acid is esterified, then the hydroxyl group(s) is esterified, and the esterified carboxyl group(s) is converted back to the carboxyl group(s) by cleaving the ester linkage moiety;

(3) The carboxyl group(s) of hydroxycitric acid is esterified, and the hydroxyl group(s) is esterified;

(4) The hydroxyl group(s) of hydroxycitric acid is esterified, and the carboxyl group(s) is esterified;

(5) The carboxyl group(s) of hydroxycitric acid is amidated, and the hydroxyl group(s) is esterified;

(6) The carboxyl group(s) of hydroxycitric acid is amidated, then the hydroxyl group(s) is esterified, and the amidated carboxyl group(s) is converted back to the carboxyl group by cleaving the amide linkage moiety; and (7) The hydroxyl group(s) of hydroxycitric acid is esterified, and the carboxyl group(s) is amidated.

There is no limitation on the process for producing compounds of the formula (IIa) in which $R^1$ is an acyl group of 14 to 22 carbon atoms, $R^2$ is a hydrogen atom, $R^3$ to $R^5$ are all hydrogen atoms, and $X^1$ to $X^3$ are all oxygen atoms, which are preferable compounds in the invention. For example, the production is possible by the process (1) or (2) given above using commercially available hydroxycitric acid as starting material.

In the production process (1) above, an ester of hydroxycitric acid may be obtained by esterifying hydroxycitric acid (or an alkali metal salt thereof or an alkaline earth metal salt thereof) by an established method. Specifically, for example, long-chain acyl hydroxycitrate may be synthesized by reacting a corresponding long-chain carboxylic acid with hydroxycitric acid (or an alkali metal salt thereof or an alkaline earth metal salt thereof) in an appropriate solvent in the presence of a catalyst (Tetrahedron Letters, 1970, P. 4011). Alternatively, a corresponding long-chain acyl chloride may be reacted with hydroxycitric acid (or an alkali metal salt thereof or an alkaline earth metal salt thereof) in an appropriate solvent (Chem. Rev., Vol. 52, P. 239, 1953). Still alternatively, a corresponding long-chain carboxylic acid anhydride may be reacted with hydroxycitric acid (or an alkali metal salt thereof or an alkaline earth metal salt thereof) (Organic Synthesis, Vol. 4, P. 560). Further alternatively, the production may involve an esterifying agent capable of activating a corresponding long-chain carboxylic acid, and hydroxycitric acid (or an alkali metal salt thereof or an alkaline earth metal salt thereof) (Organic Synthesis, Vol. 63, P. 183). Alternatively, a corresponding long-chain alkyl nitrile may be reacted with hydroxycitric acid (or an alkali metal salt thereof or an alkaline earth metal salt thereof) (Organic Synthesis, Vol. 1, P. 27).

Specifically, for example, the production process (2) above includes:

a first step in which hydroxycitric acid (or an alkali metal salt thereof or an alkaline earth metal salt thereof) is reacted with an alcohol (such as benzyl alcohol) in an appropriate solvent to temporarily protect (for example with resulting benzyl ester) the tri-carboxylic acid moiety of hydroxycitric acid;

a second step in which the hydroxyl groups of the compound obtained in the first step is esterified by any of the methods described above; and a third step in which ester moieties of the compound obtained in the second step are deprotected so as to cleave the ester linkage moieties formed in the first step.

The alcohols for use in the first step are not particularly limited as long as selective protection and deprotection of the carboxyl group moieties of hydroxycitric acid are possible. Examples thereof include benzyl alcohol, substituted benzyl alcohol, tert-butanol and 2,2,2-trichloroethanol, with benzyl alcohol and substituted benzyl alcohol being preferable. When the first step involves benzyl ester for protection, deprotection in the third step may be performed by catalytic reduction or the like.

There is no limitation on the process for producing compounds of the formula (IIb) in which $R^1$ is an acyl group of 14 to 22 carbon atoms, $R^2$ is a hydrogen atom, $R^3$ to $R^5$ are each a hydrogen atom or a chain hydrocarbon group of 1 to 30 carbon atoms that may have a branch or an unsaturated bond (with the proviso that $R^3$ to $R^5$ cannot be hydrogen atoms at the same time), and $X^1$ to $X^3$ are all oxygen atoms, which are preferable compounds in the invention. For example, the production is possible by any of the processes (2) to (4) using commercially available hydroxycitric acid as starting material.

In the production process (2) above, the third step treats the compound obtained in the second step so as to deprotect part of the ester moieties produced in the first step (part of the ester linkage moieties are cut).

The production process of the invention (production process (2) given above) may include other step between any of the three steps described above. For example, a step of distillation, extraction or crystallization for separation or purification of the product may be carried out between the first and the second steps or between the second and the third steps.

In the production processes discussed above, the amount of reagent may be appropriately adjusted so as to modify the hydroxyl group at the 2-position alone taking advantage of the difference in reactivity between the hydroxyl group at the 2-position and the hydroxyl group at the 3-position of hydroxycitric acid.

For the starting material being hydroxycitric acid, alkali metal salt thereof or alkaline earth metal salt thereof, the solvent used is not particularly limited as long as it can dissolve or suspend the starting material. Examples of the preferred solvents include polar solvents such as dimethylformamide (sometimes abbreviated to DMF hereinafter), dimethylsulfoxide, trisdimethylaminophosphine and water. These solvents may be used singly or in combination of two or more kinds.

For the starting material being hydroxycitric acid ester or amide, the solvent used is not particularly limited as long as it can dissolve or suspend the starting material. Examples of the preferred solvents include tetrahydrofuran (sometimes abbreviated to THF hereinafter), chloroform, dichloromethane and dioxane. These solvents may be used singly or in combination of two or more kinds.

The reaction temperature is not particularly limited but should be not more than the boiling point of the solvent used. Specifically, it is preferably in the range of −20 to 100° C., more preferably in the range of 0 to 60° C.

The reaction concentration is not particularly limited, and is preferably in the range of 0.0001 to 10 mol/dm$^3$, more preferably in the range of 0.1 to 1 mol/dm$^3$.

The reaction system is preferably made alkaline because hydroxycitric acid gives a cyclized product under acidic conditions.

This pH manipulation permits easy production of salts of the hydroxycitric acid derivatives. For example, the use of NaOH as pH adjuster affords a Na salt of the hydroxycitric acid derivative.

The reaction may be followed by purification by a known method such as recrystallization or silica gel column chromatography.

<Skin External Preparations and Cosmetics>

The skin external preparations according to the present invention may contain the hydroxycitric acid derivatives and salts thereof singly or in combination. The hydroxycitric acid derivative and/or salt thereof generally accounts for 0.01 to 20% by mass, preferably 0.05 to 12% by mass, more preferably 0.1 to 10% by mass of the skin external preparation. The skin external preparations containing the hydroxycitric acid derivative and/or salt thereof in this amount can quickly permeate the skin and produce expected effects.

In addition to the hydroxycitric acid derivatives and/or salts thereof, the skin external preparations may contain other substances conventionally added for slimming purposes, so as to achieve synergistic effects.

The fat accumulated in adipocytes is hydrolyzed into fatty acid and glycerol by hormone-sensitive lipase present in adipose tissues. The hormone-sensitive lipase is known to be activated by hormones such as epinephrines, glucagons and serotonins. This activation also takes place by substances similar to hormones in functions. Examples of the substances capable of increasing the hormone-sensitive lipase activity and suitable for use in cosmetics include plant extracts such as *ginkgo* extract, yew tree extract, hedera rhombea extract, selaginella shakotanensis extract, pharbitis purpurea extract, rosemary extract, *salvia officinalis* extract and green tea extract, and xanthine derivatives such as theophylline and caffeine.

It is also a known fact that the lipolytic activity of the hormone-sensitive lipase is enhanced by strengthening the bonding of the enzyme with fat. Examples of the substances having such functions and suitable for use in cosmetics include capsaicin and raspberry ketone.

The lipolysis by the hormone-sensitive lipase releases fatty acid into the blood as free fatty acid. Excessive free fatty acid can be a material of re-synthesis of fat, and therefore a substance capable of facilitating the breakdown of fatty acid may be added for the purpose of slimming effects. Examples of the substance capable of facilitating the fatty acid breakdown and suitable for use in cosmetics include carnitine, sesamin, grapefruit extract, pepper, fennel and tarragon.

These substances may be used singly or in combination of two or more kinds.

These substances play different roles in lipid metabolism from the hydroxycitric acid, and therefore synergistic effects can be expected. The amount of these substances is generally in the range of 0.01 to 20% by mass, preferably 0.5 to 15% by mass, more preferably 1 to 10% by mass of the skin external preparation.

In another embodiment of the skin external preparations of the present invention, the skin external preparations contain hydroxycitric acid derivatives represented by the formula (III) below and/or salts thereof:

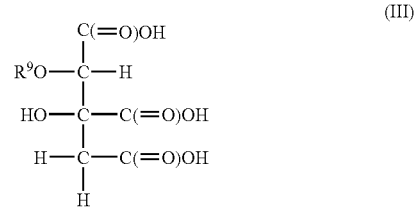

wherein $R^9$ is an acyl group comprising a cinnamic acid residue, a caffeic acid (caffeine acid) residue or a chlorogenic acid residue.

The hydroxycitric acid derivatives represented by the formula (III) are obtained by extracting natural products such as maize, coffee and garcinia xanthochymus. They have structures similar to those of the novel hydroxycitric acid derivatives of the invention. Probably because of such structures, they possess high skin affinity and/or percutaneous absorption properties and are hydrolyzed into hydroxycitric acid after absorbed in a body to provide slimming effects. Examples of the salts of the derivatives include alkali metal salts and alkaline earth metal salts.

In addition to the ingredients mentioned above, the skin external preparations of the invention may contain ingredients commonly used in skin external preparations, in amounts that do not adversely affect the effects of the invention.

Examples of such ingredients include:

hydrocarbons such as ozokerite, α-olefin oligomers, light isoparaffin, light liquid isoparaffin, squalene, squalane, synthetic squalane, vegetable squalane, ceresin, paraffin, polyethylene powder, polybutene, microcrystalline wax, liquid isoparaffin, liquid paraffin, mineral oil and vaseline;

natural waxes such as jojoba oil, carnauba wax, candelilla wax, rice bran wax, shellac, lanolin, mink oil wax, whale wax, sugarcane wax, sperm oil, beeswax and montan wax; natural fats and oils such as avocado oil, almond oil, olive oil, extra virgin olive oil, sesame oil, rice bran oil, rice oil, rice germoil, corn germoil, soybean oil, cornoil, persic oil, palm kernel oil, palm oil, castor oil, grape seed oil, cotton seed oil, coconut oil, hydrogenated coconut oil, beef tallow, hydrogenated oil, horse oil, mink oil, egg yolk oil, egg yolk fatty oil, rose hip oil, kukui nut oil, evening primrose oil, wheat germ oil, peanut oil, camellia oil, sasanqua oil, cacao butter, Japanese wax, beef bone fat, neatsfoot oil, lard, horse fat, mutton tallow, shea butter, macadamia nut oil and meadowfoam oil;

fatty acids such as lauric acid, myristic acid, palmitic acid, stearic acid, behenic acid, oleic acid, isostearic acid, 12-hydroxystearic acid, undecylenic acid and coconut fatty acid;

higher alcohols such as isostearyl alcohol, octyldodecanol, hexyldecanol, cholesterol, phytosterol, lauryl alcohol, myristyl alcohol, cetanol, stearyl alcohol, oleyl alcohol, behenyl alcohol and cetostearyl alcohol;

alkyl glyceryl ethers such as batyl alcohol, chimyl alcohol, selachyl alcohol and isostearyl glyceryl ether;

esters such as isopropyl myristate, butyl myristate, isopropyl palmitate, ethyl stearate, butyl stearate, ethyl oleate, ethyl linoleate, isopropyl linoleate, cetyl caprylate, hexyl laurate, isooctyl myristate, decyl myristate, myristyl myristate, cetyl myristate, octadecyl myristate, cetyl palmitate, stearyl stearate, decyl oleate, oleyl oleate, cetyl ricinoleate, isostearyl laurate, isotridecyl myristate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, octyldodecyl ricinoleate, ethyl isostearate, isopropyl isostearate, cetyl 2-ethylhexanoate, cetostearyl 2-ethylhexanoate, stearyl 2-ethylhexanoate, hexyl isostearate, ethylene glycol dioctanoate, ethylene glycol dioleate, propylene glycol dicaprylate, propylene glycol di(caprylate caprate), propylene glycol dicaprate, propylene glycol dioleate, neopentyl glycol dicaprate, neopentyl glycol dioctanoate, glyceryl tricaprylate, glyceryl tri-2-ethylhexanoate, glyceryl tri(caprylate caprate), glyceryl tri(caprylate caprate stearate), glyceryl triundecylate, glyceryl triisopalmitate, glyceryl triisostearate, trimethylolpropane tri-2-ethylhexanoate, trimethylolpropane triisostearate, pentaerythrityl tetra-2-ethylhexanoate, pentaerythrityl tetramyristate, pentaerythrityl tetraisostearate, diglyceryl tetraisostearate, octyldodecyl neopentanoate, isocetyl octanoate, isostearyl octanoate, 2-ethylhexyl isopelargonate, hexyldecyl dimethyloctanoate, octyldodecyl dimethyloctanoate, 2-ethylhexyl isopalmitate, isocetyl isostearate, isostearyl isostearate, octyldodecyl isostearate, lauryl lactate, myristyl lactate, cetyl lactate, octyldodecyl lactate, triethyl citrate, acetyltriethyl citrate, acetyltributyl citrate, trioctyl citrate, triisocetyl citrate, trioctyldodecyl citrate, diisostearyl malate, 2-ethylhexyl hydroxystearate, di-2-ethylhexyl succinate, diisopropyl adipate, diisobutyl adipate, dioctyl adipate, diheptylundecyl adipate, diethyl sebacate, diisopropyl sebacate, dioctyl sebacate, cholesteryl stearate, cholesteryl isostearate, cholesteryl hydroxystearate, cholesteryl oleate, dihydrocholesteryl oleate, phytosteryl isostearate, phytosteryl oleate, isocetyl 12-stearoylhydroxystearate, stearyl 12-stearoylhydroxystearate, isostearyl 12-stearoylhydroxystearate, polyoxyethylene (3) polyoxypropylene (1) cetyl ether acetate, polyoxyethylene (3) polyoxypropylene (1) isocetyl ether acetate, isononyl isononanoate, octyl isononanoate, tridecyl isononanoate and isotridecyl isononanoate;

silicone oils such as methyl polysiloxane, methylphenyl polysiloxane, methylhydrogen polysiloxane, methyl cyclopolysiloxane, octamethyl cyclotetrasiloxane, decamethyl cyclopentasiloxane, dodecamethyl cyclohexasiloxane, octamethyl trisiloxane, decamethyl tetrasiloxane, tetradecamethyl hexasiloxane, highly polymerized methyl polysiloxane, dimethyl siloxane/methyl(polyoxyethylene)siloxane/methyl(polyoxypropylene)siloxane copolymer, dimethyl siloxane/methyl(polyoxyethylene)siloxane copolymer, dimethyl siloxane/methyl(polyoxypropylene)siloxane copolymer, dimethyl siloxane/methyl cetyloxysiloxane copolymer, dimethyl siloxane/methyl stearoxysiloxane copolymer, polyether-modified silicones, alcohol-modified silicones, alkyl-modified silicones and amino-modified silicones;

polymers such as sodium alginate, carrageenan, agar, furcelleran, cyamoposis gum, pyrus cydonia seed, konjac mannan, tamarind gum, tara gum, dextrin, starch, ceratonia siliqua gum, gum arabic, ghatti gum, karaya gum, tragacanth gum, arabinogalactan, pectin, marmelo, chitosan, curdlan, xanthan gum, gellan gum, cyclodextrin, dextran, pullulan, microcrystalline cellulose, methylcellulose, ethylcellulose, hydroxyethylcellulose, hydroxypropylcellulose, hydroxypropylmethylcellulose, carboxymethylcellulose, carboxy starch, cationized cellulose, starch phosphate, cationized cyamoposis gum, carboxymethyl/hydroxypropylated cyamoposis gum, hydroxypropylated cyamoposis gum, albumin, casein, gelatin, sodium polyacrylate, polyacrylic acid amide, carboxyvinyl polymers, polyethyleneimine, highly polymerized polyethylene glycol, polyvinyl alcohol, polyvinylpyrrolidone, polyvinyl ether, polyacrylamide, acrylic acid polymers, methacrylic acid polymers, maleic acid polymers, vinylpyridine polymers, ethylene/acrylic acid copolymers, vinylpyrrolidone polymers, vinyl alcohol/vinylpyrrolidone copolymers, nitrogen-substituted acrylamide polymers, amino-modified silicones, cationized polymers, dimethylacryl ammonium polymers, acrylic acid-based anionic polymers, methacrylic acid-based anionic polymers, modified silicones, acrylic acid/alkyl($C_{10-30}$) methacrylate copolymers and polyoxyethylene/polyoxypropylene copolymer;

monoalcohols such as ethanol, isopropyl alcohol, 1-butanol, 2-butanol and benzyl alcohol;

polyhydric alcohols such as ethylene glycol, diethylene glycol, polyethylene glycol, propylene glycol, polypropylene glycol, glycerol, diglycerol, polyglycerol, 1,3-butanediol, triethylene glycol, dipropylene glycol, 3-methyl-1,3-butanediol, 1,2-pentanediol, 1,4-pentanediol, 1,5-pentanediol, 2,4-pentanediol, 2-methyl-2,4-pentanediol, 3-methyl-1,5-pentanediol, 1,2-hexanediol and 1,6-hexanediol;

anionic surfactants such as coconut fatty acid potassium, coconut fatty acid sodium, coconut fatty acid triethanolamine, potassium laurate, sodium laurate, triethanolamine laurate, potassium myristate, sodium myristate, isopropanolamine myristate, potassium palmitate, sodium palmitate, isopropanolamine palmitate, potassium stearate, sodium stearate, triethanolamine stearate, potassium oleate, sodium oleate, castor oil fatty acid sodium, zinc undecylenate, zinc laurate, zinc myristate, magnesium myristate, zinc palmitate, zinc stearate, calcium stearate, magnesium stearate, aluminum stearate, calcium myristate, magnesium myristate, aluminum dimyristate, aluminum isostearate, polyoxyethylene laurylether acetic acid, sodium polyoxyethylene laurylether acetate, polyoxyethylene tridecylether acetic acid, sodium polyoxyethylene tridecylether acetate, sodium stearoyl lactate, sodium isostearoyl lactate, sodium lauroylsarcosine, coconut fatty acid sarcosine, sodium coconut fatty acid sarcosine, coconut fatty acid sarcosine triethanolamine, lauroyl sarcosine, potassium lauroyl sarcosine, lauroyl sarcosine triethanolamine, oleyl sarcosine, sodium myristoyl sarcosine, sodium stearoyl glutamate, coconut fatty acid acylglutamic acid, potassium coconut fatty acid acylglutamate, sodium coconut fatty acid acylglutamate, coconut fatty acid acylglutamate triethanolamine, lauroyl acylglutamic acid, potassium lauroyl acylglutamate, sodium lauroyl acylglutamate, lauroyl acylglutamate triethanolamine, myristoyl acylglutamic acid, potassium myristoyl acylglutamate, sodium myristoyl acylglutamate, stearoyl acylglutamic acid, potassium stearoyl acylglutamate, disodium stearoyl acylglutamate, sodium hydrogenated tallow fatty acid acylglutamate, sodium coconut fatty acid/hydrogenated tallow fatty acid acylglutamate, sodium coconut fatty acid methylalanine, lauroyl methylalanine, sodium lauroyl methylalanine, lauroyl methylalanine triethanolamine, sodium myristoyl methylalanine, sodium lauroylmethyl taurine, potassium coconut fatty acid methyltaurine, sodium coconut fatty acid methyltaurine, magnesium coconut fatty acid methyltaurine, sodium myristoyl methyltaurine, sodium palmitoyl methyltaurine, sodium stearoyl methyltaurine, sodium oleoyl methyltaurine, sodium alkanesulfonate, sodium tetradecenesulfonate, dioctylsodiumsulfosuccinate, disodium lauryl sulfosuccinate, sodium coconut fatty acid ethylester sulfonate, sodium laurylsulfate, triethanolamine laurylsulfate, sodium cetyl sulfate, triethanolamine alkylsulfates (11,13, 15), sodium alkylsulfates (12,13), triethanolamine alkylsulfates (12,13), ammonium alkylsulfates (12,14,16), diethanolamine alkylsulfates (12,13), triethanolamine alkylsulfates (12-14), triethanolamine alkylsulfates (12-15), magnesium triethanolamine cocoalkylsulfate, ammonium laurylsulfate, potassium laurylsulfate, magnesium laurylsulfate, monoethanolamine laurylsulfate, diethanolamine laurylsulfate, sodium myristylsulfate, sodium stearylsulfate, sodium oleylsulfate, triethanolamine oleylsulfate, sodium polyoxyethylene laurylether sulfate, triethanolamine polyoxyethylene laurylether sulfate, sodium polyoxyethylene (1) alkyl (11,13,15) ether sulfate, triethanolamine polyoxyethylene (1) alkyl (11, 13,15) ether sulfate, sodium polyoxyethylene (3) alkyl (11-15) ether sulfate, sodium polyoxyethylene (2) alkyl (12, 13) ether sulfate, sodium polyoxyethylene (3) alkyl (12-14) ether sulfate, sodium polyoxyethylene (3) alkyl (12-15) ether sulfate, sodium polyoxyethylene (2) laurylether sulfate, sodium polyoxyethylene (3) myristylether sulfate, sodium higher fatty acid alkanolamide sulfate, laurylphosphoric acid, sodium laurylphosphate, potassium cetylphosphate, diethanolamine cetylphosphate, polyoxyethylene oleylether phosphoric acid, polyoxyethylene laurylether phosphoric acid, sodium polyoxyethylene laurylether phosphate, polyoxyethylene cetylether phosphoric acid, sodium polyoxyethylene cetylether phosphate, polyoxyethylene stearylether phosphoric acid, sodium polyoxyethylene oleylether phosphate, polyoxyethylene alkylphenyl ether phosphoric acid, sodium polyoxyethylene alkylphenyl ether phosphate, triethanolamine polyoxyethylene alkylphenyl ether phosphate, polyoxyethylene octylether phosphoric acid, polyoxyethylene (10) alkyl (12,13) ether phosphoric acid, polyoxyethylene alkyl (12-15) ether phosphoric acid, polyoxyethylene alkyl (12-16) ether phosphoric acid, triethanolamine polyoxyethylene laurylether phosphate and diethanolamine polyoxyethylene oleylether phosphate;

cationic surfactants such as dioctylamine, dimethylstearylamine, trilaurylamine, stearic acid diethylaminoethylamide, lauryltrimethylammonium chloride, cetyltrimethylammonium chloride, cetyltrimethylammonium bromide, cetyltrimethylammonium saccharin, stearyltrimethylammonium chloride, alkyl (20-22) trimethylammonium chloride, lauryltrimethylammonium bromide, alkyl (16,18) trimethylammonium chloride, stearyltrimethylammonium bromide, stearyltrimethylammonium saccharin, alkyl (28) trimethylammonium chloride, di(polyoxyethylene)oleylmethylammonium chloride (2EO), dipolyoxyethylenestearylmethylammonium chloride, polyoxyethylene (1) polyoxypropylene (25) diethylmethylammonium chloride, tri(polyoxyethylene)stearylammonium chloride (5EO), distearyldimethylammonium chloride, dialkyl (12-15) dimethylammonium chloride, dialkyl (12-18) dimethylammonium chloride, dialkyl (14-18) dimethylammonium chloride, dicocoyldimethylammonium chloride, dicetyldimethylammonium chloride, isostearyllauryldimethylammonium chloride, benzalkonium chloride, myristyldimethylbenzylammonium chloride, lauryldimethyl(ethylbenzyl)ammonium chloride, stearyldimethylbenzylammonium chloride, laurylpyridinium chloride, cetylpyridinium chloride, lauroylcolaminoformylmethylpyridinium chloride, stearoylcolaminoformylmethylpyridinium chloride, alkylisoquinolium bromide, methylbenzethonium chloride and benzethonium chloride;

amphoteric surfactants such as 2-alkyl-N-carboxymethyl-N-hydroxyethyl imidazolinium betaine, alkyldiaminoethylglycine hydrochloride, sodium lauryldiaminoethylglycine, sodium undecylhydroxyethylimidazolium betaine, undecyl-N-carboxymethylimidazoliumbetaine, disodium coconut fatty acid acyl-N-carboxyethyl-N-hydroxyethylethylenediamine, disodium coconut fatty acid acyl-N-carboxyethoxyethyl-N-carboxyethylethylenediamine, disodium coconut fatty acid acyl-N-carboxymethyl-N-carboxymethylethylenediamine, sodium laurylaminopropionate, sodium laurylaminodipropionate, triethanolamine laurylaminopropionate, sodium palm oil fatty acid acyl-N-carboxyethyl-N-hydroxyethylethylenediamine, betaine lauryldimethylaminoacetate, betaine coconut oil alkyldimethylaminoacetic acid, betaine stearyldimethylaminoacetate, sodium stearyldimethyl betaine, coconut fatty acid amidopropylbetaine, palm oil fatty acid amidopropylbetaine, lauric acid amide betaine propylacetate, amidopropylbetaine ricinoleate, stearyldihydroxyethyl betaine and laurylhydroxysulfobetaine;

nonionic surfactants such as polyoxyethylene (10) alkyl (12, 13) ether, polyoxyethylene lauryl ether, polyoxyethylene cetyl ether, polyoxyethylene stearyl ether, polyoxyethylene oleyl ether, polyoxyethylene (3,7,12) alkyl (12-14) ether, polyoxyethylene tridecyl ether, polyoxyethylene myristyl ether, polyoxyethylene-sec-alkyl (14) ether, polyoxyethylene isocetyl ether, polyoxyethylene cetostearyl ether, polyoxyethylene (2,10,20) isostearyl ether, polyoxyethylene oleylcetyl ether, polyoxyethylene (20) aralkyl ether, polyoxyethylene octyldodecyl ether, polyoxyethylene behenyl ether, polyoxyethylene octylphenyl ether, polyoxyethylene nonylphenyl ether, polyoxyethylene dinonylphenyl ether, polyoxyethylene (1) polyoxypropylene (1,2,4,8) cetyl ether, polyoxyethylene (5) polyoxypropylene (1,2,4,8) cetyl ether, polyoxyethylene (10) polyoxypropylene (1,2,4,8) cetyl ether, polyoxyethylene (20) polyoxypropylene (1,2,4,8) cetyl ether, polyoxyethylene polyoxypropylene lauryl ether, polyoxyethylene (3) polyoxypropylene (34) stearyl ether, polyoxyethylene (4) polyoxypropylene (30) stearyl ether, polyoxyethylene (34) polyoxypropylene (23) stearyl ether, polyoxyethylene polyoxypropylene cetyl ether, polyoxyethylene polyoxypropylene decyltetradecyl ether, polyethylene glycol monolaurate, ethylene glycol monostearate, polyethylene glycol monostearate, polyethylene glycol monooleate, ethylene glycol fatty acid ester, self-emulsifiable ethylene glycol monostearate, diethylene glycol laurate, polyethylene glycol myristate, polyethylene glycol palmitate, diethylene glycol stearate, self-emulsifiable polyethylene glycol (2) monostearate, polyethylene glycol isostearate, ethylene glycol dioctanoate, diethylene glycol dilaurate, polyethylene glycol dilaurate, polyethylene glycol (150) dipalmitate, ethylene glycol distearate, diethylene glycol distearate, polyethylene glycol distearate, ethylene glycol dioleate, polyethylene glycol dioleate, polyethylene glycol diricinoleate, polyoxyethylene (20) sorbitan monolaurate, polyoxyethylene (20) sorbitan monopalmitate, polyoxyethylene (6) sorbitan monostearate, polyoxyethylene (20) sorbitan monostearate, polyoxyethylene (20) sorbitan tristearate, polyoxyethylene (6) sorbitan monooleate, polyoxyethylene (20) sorbitan monooleate, polyoxyethylene (20) sorbitantrioleate, polyoxyethylene (20) coconut fatty acid sorbitan, polyoxyethylene (10-80) sorbitan monolaurate, polyoxyethylene sorbitan tristearate, polyoxyethylene (20) sorbitan isostearate, polyoxyethylene (150) sorbitan tristearate, polyoxyethylene castor oil, polyoxyethylene hydrogenated castor oil, polyoxyethylene (10) hydrogenated castor oil, polyoxyethylene (20) hydrogenated castor oil, polyoxyethylene (40) hydrogenated castor oil, polyoxyethylene (50) hydrogenated castor oil, polyoxyethylene (60) hydrogenated castor oil, lipophilic glyceryl monostearate, lipophilic glyceryl monooleate, self-emulsifiable glyceryl monostearate, coconut fatty acid glyceryl, glyceryl laurate, glyceryl myristate, glyceryl isostearate, glyceryl ricinoleate, glyceryl monohydroxystearate, glyceryl oleate, glyceryl linoleate, glyceryl erucate, glyceryl behenate, wheat germ oil fatty acid glyceride, safflower oil fatty acid glyceryl, hydrogenated soybean fatty acid glyceryl, saturated fatty acid glyceride, cotton seed oil fatty acid glyceryl, monoisostearic acid glyceryl monomyristate, monotallow fatty acid glyceride, glyceryl monolanolin fatty acid, glyceryl sesquioleate, glyceryl distearate, glyceryl diisostearate, glyceryl diarachidate, sorbitan monolaurate, sorbitan monopalmitate, sorbitan monostearate, sorbitan monoisostearate, sorbitan monooleate, sorbitan sesquistearate, sorbitan sesquioleate, sorbitan tristearate, sorbitan trioleate, coconut fatty acid sorbitan, sorbitan isostearate, sorbitan sesquiisostearate, sorbitan distearate, diglyceryl isopalmitate, poly (4-10) glyceryl monolaurate, poly (10) glyceryl monomyristate, poly (2-10) glyceryl monostearate, poly (2-10) glyceryl monoisostearate, poly (2-10) glyceryl monooleate, diglyceryl sesquioleate, poly (2-10) glyceryl diisostearate, poly (6-10) glyceryl distearate, diglyceryl triisostearate, poly (10) glyceryl tristearate, poly (10) glyceryl trioleate, poly (2) glyceryl tetraisostearate, decaglyceryl pentastearate, poly (6-10) glycerylpentaoleate, poly (10) glyceryl heptastearate, decaglyceryl decastearate, poly (10) glyceryl decaoleate, condensed poly (6) glyceryl ricinoleate, sucrose fatty acid ester, sucrose coconut fatty acid ester, alkyl glucoside, coconut oil alkyldimethylamine oxide, lauryldimethylamine oxide, dihydroxyethyllauryldimethylamine oxide, stearyldimethylamine oxide, oleyldimethylamine oxide and polyoxyethylene coconut oil alkyldimethylamine oxide;

natural surfactants such as saponin, lecithin, soybean phospholipid, hydrogenated soybean phospholipid, soybean lysophospholipid, hydrogenated soybean lysophospholipid, egg yolk lecithin, hydrogenated egg yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid and mannosylerythritol lipid;

ultraviolet light absorbers, including para-aminobenzoic acid, para-aminobenzoic acid derivatives such as ethyl para-aminobenzoate, glyceryl para-aminobenzoate, amyl para-dimethylaminobenzoate and 2-ethylhexyl para-dimethylaminobenzoate, cinnamic acid derivatives such as benzyl cinnamate, dipara-methoxy cinnamic acid glyceryl mono-2-ethylhexanoate, methyl 2,4-diisopropylcinnamate, ethyl 2,4-diisopropylcinnamate, potassium para-methoxycinnamate, sodium para-methoxycinnamate, isopropyl para-methoxycinnamate, 2-ethylhexyl para-methoxycinnamate, 2-ethoxy-ethyl para-methoxycinnamate and ethyl para-ethoxycinnamate, urocanic acid, urocanic acid derivatives such as ethyl urocanate, benzophenone derivatives such as 2,4-dihydroxybenzophenone, 2,2',4,4'-tetrahydroxybenzophenone, 2-hydroxy-4-methoxy-5-sulfobenzophenone sodium, 2-hydroxy-4-methoxybenzophenone-5-sulfonic acid, 2-hydroxy-4-methoxybenzophenone, 2,2'-dihydroxy-4,4'-dimethoxybenzophenone and 2,2'-dihydroxy-4,4'-dimethoxy-5-sulfobenzophenone sodium, salicylic acid derivatives such as ethylene glycol salicylate, 2-ethylhexyl salicylate, phenyl salicylate, benzyl salicylate, p-tert-butylphenyl salicylate, homomenthyl salicylate and 3,3,5-trimethylcyclohexyl salicylate, 2-(2'-hydroxy-5'-methoxyphenyl)benzotriazole and 4-tert-butyl-4'-methoxybenzoylmethane;

powders and color materials, including kaolin, silicic anhydride, aluminum magnesium silicate, sericite, talc, boron nitride, mica, montmorillonite, hemp cellulose powder, wheat starch, silk powder, cornstarch, nitro dye, azo dye, nitroso dye, triphenylmethane dye, xanthene dye, quinoline dye, anthraquinone dye, indigo dye, pyrene dye, phthalocyanine dye, natural dyes such as flavonoid, quinone, porphyrin, water-soluble annatto, squid ink powder, caramel, guaiazulene, gardenia blue, gardenia yellow, cochineal, shikonin, sodium copper chlorophyllin, paprika dye, safflower red, safflower yellow, laccaic acid and riboflavin butyrate, carbon black, yellow iron oxide, black iron oxide, red iron oxide, iron blue, ultramarine blue, zinc oxide, chromium oxide, titanium oxide, black titanium oxide, zirconium oxide, chromium hydroxide, alumina, magnesium oxide, barium sulfate, aluminum hydroxide, calcium carbonate, lithium cobalt titanate, manganese violet and pearl pigment;

plant extracts such as angelica keiskei extract, gambir extract, avocado extract, hydrangea serrata leaf extract, gynostemma pentaphyllum extract, althea extract, arnica extract, oil-soluble arnica extract, almond extract, aloe extract, styrax benzoin resin extract, *urtica* extract, orris root extract, *curcuma* extract, rose fruit extract, *echinacea* leaf extract, scutellaria baicalensis root extract, phellodendron bark extract, coptis rhizome extract, *hordeum vulgare* seed extract, gumbo extract, *hypericum erectum* extract, oil-soluble *hypericum erectum* extract, *lamium album* flower extract, oil-soluble *lamium album* flower extract, ononis extract, nasturtium officinale extract, orange flower water, kaki tannin, puerariae radix extract, valerian extract, cattail extract, chamomilla extract, oil-soluble chamomilla extract, chamomilla water, oat extract, carrot extract, oil-soluble carrot extract, carrot oil, *artemisia capillaris* extract, licorice extract, licorice extract powder, licorice flavonoid, cantharis tincture, raspberry extract, kiwi extract, cinchona bark extract, cucumber extract, apricot kernel extract, quince seed extract, gardenia extract, sasa veitchii extract, sophora angustifolia extract, walnut shell extract, clematis extract, brown sugar extract, *chlorella* extract, mulberry extract, cinnamon bark extract, gentian extract, *geranium* herb extract, spatterdock extract, arctium lappa root extract, oil-soluble arctium lappa root extract, wheat germ extract, hydrolyzed wheat powder, rice bran extract, rice bran fermentation extract, comfrey extract, asiasarum root extract, saffron extract, *saponaria officinalis* extract, oil-soluble *salvia* extract, crataegus cuneata fruit extract, xanthoxylum extract, shiitake mushroom extract, shiitake mushroom extract powder, rehmannia glutinosa extract, sycon extract, oil-soluble sycon extract, Japanese basil extract, linden extract, oil-soluble linden extract, filipendula multijuga extract, peony root extract, coix lacryma-jobi seed extract, ginger extract, oil-soluble ginger extract, ginger tincture, acorus calamus root extract, *betula alba* extract, oil-soluble *betula alba* extract, *betula alba* sap, lonicera extract, equisetum arvense extract, oil-soluble equisetum arvense extract, scordinin, stevia extract, crataegus oxyacantha extract, *sambucus nigra* flower extract, *juniperus communis* extract, achillea millefolium extract, oil-soluble achillea millefolium extract, mentha piperita extract, sage extract, oil-soluble sage extract, sage water, mallow extract, celery extract, cnidium officinale extract, cnidium officinale water, swertia japonica extract, soybean extract, jujube extract, thyme extract, *camellia sinensis* leaf extract, *camellia sinensis* dry distillate, *camellia sinensis* seed extract, clove flower extract, citrus unshiu peel extract, *camellia japonica* seed extract, *centella asiatica* extract, oil-soluble juglans regia extract, duke extract, *terminalia* extract, angelica acutiloba extract, oil-soluble angelica acutiloba extract, angelica acutiloba water, calendula officinalis flower extract, oil-soluble calendula officinalis flower extract, soymilk powder, *prunus persica* extract, *citrus aurantium amara* extract, houttuynia cordata extract, tomato extract, potentilla erecta root extract, natto extract, *ginseng* extract, oil-soluble *ginseng* extract, garlic extract, rosa canina fruit extract, oil-soluble rosa canina fruit extract, malt extract, malt root extract, ophiopogon tuber extract, parsley extract, *hordeum vulgare* leaf juice concentrate, distilled peppermint water, hamamelis water, rosa centifolia flower extract, *parietaria* extract, isodonis japonicus extract, *eriobotrya japonica* leaf extract, oil-soluble *eriobotrya japonica* leaf extract, coltsfoot flower extract, poria cocos extract, *ruscus aculeatus* root extract, *ruscus aculeatus* root extract powder, grape extract, grape leaf extract, grape water, hayflower extract, *luffa cylindrica* fruit extract, *luffa cylindrica* fruit water, safflower extract, oil-soluble tilia platyphyllos flower extract, tilia platyphyllos flower water, paeonia suffruticosa root extract, hops extract, oil-soluble hops extract, pinus sylvestris cone extract, *silybum marianum* fruit extract, horse chestnut extract, oil-soluble horse chestnut extract, sapindus mukurossi peel extract, melissa officinalis leaf extract, melilotus officinalis extract, peach leaf extract, oil-soluble peach leaf extract, bean-sprouts extract, centaurea cyanus flower extract, centaurea cyanus flower water, eucalyptus extract, saxifraga sarmentosa extract, *lilium candidum* bulb extract, coix lacryma jobi seed extract, oil-soluble coix lacryma jobi seed extract, *artemisia princeps* extract, *artemisia princeps* water, lavender extract, lavender water, apple extract, *ganoderma lucidum* extract, lettuce extract, astragalus sinicus extract, rose water, anthemis nobilis flower extract and sanguisorba officinalis root extract;

amino acids and peptides such as glycine, valine, leucine, isoleucine, serine, threonine, phenylalanine, tyrosin, tryptophan, cystine, cysteine, methionine, hydroxyproline, aspartic acid, asparagine, glutamic acid, glutamine, histidine, γ-aminobutyric acid, DL-pyrrolidonecarboxylic acid, ε-aminocaproic acid, hydrolyzed elastin, water-soluble elastin, hydrolyzed collagen, water-soluble collagen, casein, glutathione, wheat peptide and soybean peptide;

vitamins and vitamin affecters, including vitamin A such as retinol, retinal, retinoic acid, retinol acetate and retinol palmitate, carotenoids such as α-carotene, β-carotene, γ-carotene, δ-carotene, lycopene, zeaxanthin, cryptoxanthin, echinenone and astaxanthin, vitamin B1 such as thiamines, vitamin B2 such as riboflavin, vitamin B6 such as pyridoxine, pyridoxal and pyridoxamine, vitamin B12 such as cyanocobalamin, folic acids, nicotinic acid, nicotinic acid amide, pantothenic acids, biotins, vitamin C such as L-ascorbic acid, sodium L-ascorbate, L-ascorbyl stearate, L-ascorbyl palmitate, L-ascorbyl dipalmitate, L-ascorbyl tetraisopalmitate, disodium L-ascorbate sulfate, L-ascorbylmagnesiumphosphate, L-ascorbyl sodium phosphate, 2-phosphate ascorbate and 2-glucoside L-ascorbate, vitamin D such as ergocalciferol and cholecalciferol, vitamin E such as d-α-tocopherol, DL-α-tocopherol, dl-α-tocopherol acetate, dl-α-tocopherol succinate, β-tocopherol, γ-tocopherol and d-δ-tocopherol, ubiquinones, vitamin K, ferulic acid, γ-oryzanol, α-lipoic acid and orotic acid;

antiseptics such as benzoic acid, sodium benzoate, undecylenic acid, salicylic acid, sorbic acid, potassium sorbate, dehydroacetic acid, sodium dehydroacetate, isobutyl para-oxybenzoate, isopropyl para-oxybenzoate, ethyl para-oxybenzoate, butyl para-oxybenzoate, propyl para-oxybenzoate, benzyl para-oxybenzoate, methyl para-oxybenzoate, methyl sodium para-oxybenzoate, phenoxyethanol, photosensitive agent No. 101, photosensitive agent No. 201 and photosensitive agent No. 401;

antioxidants such as butylhydroxyanisole, butylhydroxytoluene, propyl gallate, erythorbic acid, sodium erythorbate, para-hydroxyanisole and octyl gallate;

sequestering agents such as trisodium ethylenediaminehydroxyethyltriacetate, edetic acid, disodium edetate, trisodium edetate, tetrasodium edetate, sodium citrate, gluconic acid, phytic acid, sodium polyphosphate and sodium metaphosphate;

moisturizers such as hyaluronic acid, sodium hyaluronate, sodium chondroitinsulfate, sodium lactate, sodium pyrrolidonecarboxylate, betaine, lactic acid bacteria culture solution, yeast extract and ceramide;

antiinflammatory agents such as glycyrrhizinic acid, trisodium glycyrrhizinate, dipotassium glycyrrhizinate, monoammonium glycyrrhizinate, β-glycyrrhetinic acid, glycerol glycyrrhetinate, stearyl glycyrrhetinate, lysozyme chloride, hydrocortisone and allantoin;

pH adjusters such as sodium hydroxide, potassium hydroxide and triethanolamine;

salts such as sodium chloride, potassium chloride, magnesium chloride and sodium sulfate;

α-hydroxy acids such as citric acid, glycolic acid, tartaric acid and lactic acid;

whitening agents such as arbutin, α-arbutin and placental extract;

essential oils such as angelica oil, ylang ylang oil, elemi oil, German chamomile oil, anthemis nobilis oil, cardamom oil, calamus oil, galbanum oil, camphor oil, carrot seed oil, clary sage oil, clove oil, cinnamon bark oil, coriander oil, cypress oil, sandalwood oil, cedarwood oil, citronella oil, cinnamon leaf oil, jasmine absolute, juniper berry oil, ginger extract, spearmint oil, sage oil, cedar oil, geranium oil, thyme oil, tea tree oil, nutmeg oil, niaouli oil, neroli oil, pine oil, basil oil, peppermint oil, patchouli oil, palmarosa oil, fennel oil, petitgrain oil, black pepper oil, frankincense oil, vetivert oil, peppermint oil, bergamot oil, benzoin oil, aniba rosaeodora oil, marjoram oil, myrrh oil, melissa oil, eucalyptus oil, ravensara oil, lavandin oil, lavender oil, lindane oil, rose oil, rosewood oil, rosemary oil and lovage oil;

terpenes such as pinene, terpinene, terpinolene, myrcene and longifolene;

perfumes and water.

The skin external preparations in a broad sense include any kinds of preparations that can be used in contact with skin. Examples thereof include skin milks, skin creams, foundation creams, massage creams, cleansing creams, shaving creams, cleansing foams, skin toners, lotions, packs, lipsticks, rouges, eye shadows, manicures, soaps, body shampoos, hand soaps, shampoos, conditioners, hair tonics, treatment conditioners, hair creams, hair sprays, hair growth tonics, baldness remedies, hairdyes, styling spritz, depilatories, antidandruff hair lotions, toothpastes, denture adhesives, mouthwashes, permanent wave agents, curling agents, styling agents, ointments, adhesive skin patches, tape agents, bath agents, antiperspirants and sunscreen agents. The external preparations are particularly suitable for use as cosmetics. The external preparations can be used regardless of user's gender and age, and can be used for animal skin as well as human skin.

The cosmetics according to the present invention contain the skin external preparations as described above. The cosmetics may contain other ingredients (of the ingredients mentioned above for use in skin external preparations) that are generally employable in cosmetics. Further, the cosmetics may contain existing cosmetic ingredients in amounts that do not adversely affect the effects of the invention.

For example, any of the cosmetic ingredients listed in the following documents are employable: The Japanese Standards of Cosmetic Ingredients 2nd edition (edited by Society of Japanese Pharmacopoeia and published by Yakuji Nippo, Ltd. (1984)), The Japanese Cosmetic Ingredients Codex (edited by Ministry of Health and Welfare, Pharmaceutical Examination Division and published by Yakuji Nippo, Ltd.

(1993) ), Supplement to The Japanese Cosmetic Ingredients Codex (edited by Ministry of Health and Welfare, Pharmaceutical Examination Division and published by Yakuji Nippo, Ltd. (1993)), The Comprehensive Licensing Standards of Cosmetics by Category (edited by Ministry of Health and Welfare, Pharmaceutical Examination Division and published by Yakuji Nippo, Ltd. (1993)), The Japanese Cosmetic Ingredients Codex by Category (edited by Ministry of Health and Welfare, Pharmaceutical Examination Division and published by Yakuji Nippo, Ltd. (1997)), Dictionary of Cosmetic Ingredients (Nikko Chemicals., Co. Ltd. (1991)), and Latest Cosmetic Functional Materials 300 (CMC Publishing Co., Ltd. (2002)).

The amount of the hydroxycitric acid derivatives and/or salts thereof in the cosmetics is preferably the same as in the skin external preparations described above.

The skin external preparations and cosmetics of the invention may be produced by dissolving, mixing or dispersing the specified amounts of the aforementioned ingredients by an established method depending on the embodiment. The skin external preparations and cosmetics may be in any states such as solid, liquid, semisolid and gas, and may be in any forms including powder, granules, tablets, gels and foams, although not particularly limited thereto.

EXAMPLES

Hereinbelow, the present invention will be described in greater detail by examples. However, it should be construed that the invention is not limited thereto.

The determination of hydroxycitric acid and hydroxycitric acid derivative was performed by the standard addition method using liquid chromatography mass spectrometry (hereinafter LC/MS).
Liquid chromatograph: Agilent 1100 series
Column: Shodex OHpak SB-802.5 HQ
Column temperature: 40° C.
Eluting solution: 0.02 M aqueous ammonium acetate solution/acetonitrile=75/25 (V/V)
Eluting solution flow rate: 0.8 ml/min
Sample injection amount: 100 μl (an autosampler was used)
Mass spectrometer: Thermoquest LCQ Advantage
Ionization method: Electrospray ionization (ESI)
Measurement mode: Selective ion monitoring (SIM)
Monitoring ions: m/z 207 (for hydroxycitric acid), m/z 445 (for hydroxycitric acid-2-palmitate)

Example 1

Synthesis of hydroxycitric acid-2-palmitate sodium salt (1) Synthesis of hydroxycitric acid tribenzyl ester A 200-ml evaporation flask was charged with 2.96 g (10.1 mmol) of calcium hydroxycitrate, 5.86 g (30.8 mmol) of toluenesulfonic acid monohydrate, 10 g (92.5 mmol) of benzyl alcohol and 20 ml of toluene. These were stirred under reflux for 4 hours with azeotropic water removal. After cooled naturally, the mixture was combined with 50 ml of ethyl acetate, and these were stirred well.

The resultant mixture in small portions was introduced with stirring into a 500-ml beaker containing 100 ml of a 5% by mass aqueous solution of sodium hydrogencarbonate. The insolubles were removed, the aqueous phase was separated, and the organic phase was washed with water and was dried over anhydrous sodium sulfate. The solvent and benzyl alcohol were evaporated in vacuo, and the residue was subjected to silica gel column chromatography. Elution using a 5:1 mixture of hexane and ethyl acetate gave 1.96 g of the objective compound as a white solid (40% yield).

(2) Synthesis of hydroxycitric acid tribenzyl ester-2-palmitate

A 50-ml evaporation flask was charged with 239 mg (0.50 mmol) of hydroxycitric acid tribenzyl ester synthesized in (1) above, 5 ml of THF and 165 mg (0.60 mmol) of palmitoyl chloride. The flask was further charged with a solution of 61 mg (0.60 mmol) of triethylamine in 2 ml of THF while cooled with ice. Stirring was performed for 30 minutes at the temperature and for 2 hours at room temperature.

To the reaction liquid, 100 ml and 50 ml of ethyl acetate and water, respectively, were added. The organic phase was washed in the usual way and was dried over anhydrous sodium sulfate. The solvent was evaporated in vacuo, and the residue was subjected to silica gel column chromatography. Elution using a 10:1 mixture of hexane and ethyl acetate gave 330 mg of the objective compound as a white solid (92% yield).

(3) Synthesis of hydroxycitric acid-2-palmitate

A 50-ml evaporation flask was charged with 300 mg (0.42 mmol) of hydroxycitric acid tribenzyl ester-2-palmitate synthesized in (2) above, 5 ml of ethanol and 5 ml of DMF. Subsequently, 40 mg of 10% by mass-palladium activated carbon was added as a catalyst, and catalytic reduction was carried out for 2 hours. The catalyst was filtered off, and the solvent was evaporated in vacuo. To the residue, hexane was added. The solid precipitated was filtered to give 175 mg of the objective compound as a white solid (84% yield).

The structure of the compound obtained was identified by the $^1$H-NMR spectrum given below:
$^1$H-NMR (270 MHz, DMSO-$D_6$, ppm): 5.0 (s, 1H, CH), 3.2-3.8 (br, 4H, OH, COOH), 2.7-3.0 (dd, 2H, —$CH_2$COOH), 2.0-2.2 (m, 2H, —$CH_2$COOC—), 1.0-1.5 (m, 26H, —$(CH_2)_{13}$—), 0.8-0.9 (t, 3H, $CH_3$—)

(4) Synthesis of hydroxycitric acid-2-palmitate sodium salt

A 500-ml evaporation flask was charged with 10 g (22.4 mmol) of hydroxycitric acid-2-palmitate synthesized as described in (3) above, and 200 ml of distilled water was added to form a suspension. The suspension was combined with 2.15 g (53.8 mmol) of sodium hydroxide, and the mixture was stirred until it became transparent. The thus-formed solution was concentrated and dried in an evaporator, and 12.1 g of the objective compound resulted (99% yield).

Example 2

Synthesis of hydroxycitric acid-2-myristate sodium salt (1) Synthesis of hydroxycitric acid tribenzyl ester-2-myristate Synthesis was made in a similar manner as in Example 1 (2), using 330 mg (0.69 mmol) of hydroxycitric acid tribenzyl ester synthesized in a similar manner as in Example 1 (1), 5 ml of THF, 340 mg (1.38 mmol) of myristoyl chloride and 203 mg (2.00 mmol) of triethylamine. Thus, 350 mg of the objective compound was obtained as a white solid (74% yield).

(2) Synthesis of hydroxycitric acid-2-myristate

A 50-ml evaporation flask was charged with 300 mg (0.43 mmol) of hydroxycitric acid tribenzyl ester-2-myristate synthesized in (1) above, 5 ml of THF and 5 ml of ethanol, and synthesis was made in a similar manner as in Example 1 (3). Thus, 180 mg of the objective compound was obtained as a white solid (99% yield).

The structure of the compound obtained was identified by the $^1$H-NMR spectrum given below:

$^1$H-NMR (500 MHz, DMSO-D$_6$, ppm): 5.0 (s, 1H, CH), 3.2-3.8 (br, 4H, OH, COOH), 2.9 (s, 2H, —CH$_2$COOH), 2.2-2.3 (m, 2H, —CH$_2$COOC—), 1.1-1.5 (m, 22H, —(CH$_2$)$_{11}$—), 0.8-0.9 (t, 3H, CH$_3$—)

(3) Synthesis of hydroxycitric acid-2-myristate sodium salt

Synthesis was made in a similar manner as in Example 1 (4), except that 10 g of hydroxycitric acid-2-palmitate was replaced with 9.4 g of hydroxycitric acid-2-myristate synthesized as described in (2) above. Thus, 11.4 g of the objective compound resulted (99% yield).

Example 3

Synthesis of hydroxycitric acid-2-laurate sodium salt (1) Synthesis of hydroxycitric acid tribenzyl ester-2-laurate Synthesis was made in a similar manner as in Example 1 (2), using 479 mg (1.00 mmol) of hydroxycitric acid tribenzyl ester synthesized in a similar manner as in Example 1 (1), 5 ml of THF, 438 mg (2.00 mmol) of lauroyl chloride and 203 mg (2.00 mmol) of triethylamine. Thus, 610 mg of the objective compound was obtained as a white solid (92% yield).

(2) Synthesis of hydroxycitric acid-2-laurate

A 50-ml evaporation flask was charged with 580 mg (0.88 mmol) of hydroxycitric acid tribenzyl ester-2-laurate synthesized in (1) above, 5 ml of THF and 5 ml of ethanol, and synthesis was made in a similar manner as in Example 1 (3). Thus, 342 mg of the objective compound was obtained as a white solid (88% yield).

The structure of the compound obtained was identified by the $^1$H-NMR spectrum given below:

$^1$H-NMR (500 MHz, DMSO-D$_6$, ppm): 5.0 (s, 1H, CH), 3.2-4.2 (br, 4H, OH, COOH), 2.9 (s, 2H, —CH$_2$COOH), 2.2-2.3 (m, 2H, —CH$_2$COOC—), 1.1-1.5 (m, 18H, —(CH$_2$)$_9$—), 0.8-0.9 (t, 3H, CH$_3$—)

(3) Synthesis of hydroxycitric acid-2-laurate sodium salt

Synthesis was made in a similar manner as in Example 1 (4), except that 10 g of hydroxycitric acid-2-palmitate was replaced with 8.7 g of hydroxycitric acid-2-laurate synthesized as described in (2) above. Thus, 10.7 g of the objective compound resulted (99% yield).

Example 4

Synthesis of hydroxycitric acid-2-caprate sodium salt (1) Synthesis of hydroxycitric acid tribenzyl ester-2-caprate Synthesis was made in a similar manner as in Example 1 (2), using 479 mg (1.00 mmol) of hydroxycitric acid tribenzyl ester synthesized in a similar manner as in Example 1 (1), 5 ml of THF, 382 mg (2.00 mmol) of caproyl chloride and 203 mg (2.00 mmol) of triethylamine. Thus, 570 mg of the objective compound was obtained as a white solid (90% yield).

(2) Synthesis of hydroxycitric acid-2-caprate

A 50-ml evaporation flask was charged with 520 mg (0.82 mmol) of hydroxycitric acid tribenzyl ester-2-caprate synthesized in (1) above, 5 ml of THF and 5 ml of ethanol, and synthesis was made in a similar manner as in Example 1 (3). Thus, 240 mg of the objective compound was obtained as a white solid (81% yield).

The structure of the compound obtained was identified by the $^1$H-NMR spectrum given below:

$^1$H-NMR (500 MHz, DMSO-D$_6$, ppm): 5.0 (s, 1H, CH), 3.2-4.2 (br, 4H, OH, COOH), 2.9 (s, 2H, —CH$_2$COOH), 2.2-2.3 (m, 2H, —CH$_2$COOC—), 1.1-1.5 (m, 14H, —(CH$_2$)$_7$—), 0.8-0.9 (t, 3H, CH$_3$—)

(3) Synthesis of hydroxycitric acid-2-caprate sodium salt

Synthesis was made in a similar manner as in Example 1 (4), except that 10 g of hydroxycitric acid-2-palmitate was replaced with 8.1 g of hydroxycitric acid-2-caprate synthesized as described in (2) above. Thus, 10.1 g of the objective compound resulted (99% yield).

Example 5

Synthesis of hydroxycitric acid-2-octanoate sodium salt (1) Synthesis of hydroxycitric acid tribenzyl ester-2-octanoate Synthesis was made in a similar manner as in Example 1 (2), using 479 mg (1.00 mmol) of hydroxycitric acid tribenzyl ester synthesized in a similar manner as in Example 1 (1), 5 ml of THF, 325 mg (2.00 mmol) of capryloyl chloride and 203 mg (2.00 mmol) of triethylamine. Thus, 600 mg of the objective compound was obtained as a white solid (94% yield).

(2) Synthesis of hydroxycitric acid-2-octanoate

A 50-ml evaporation flask was charged with 490 mg (0.81 mmol) of hydroxycitric acid tribenzyl ester-2-octanoate synthesized in (1) above, 5 ml of THF and 5 ml of ethanol, and synthesis was made in a similar manner as in Example 1 (3). Thus, 240 mg of the objective compound was obtained as a white solid (89% yield).

The structure of the compound obtained was identified by the $^1$H-NMR spectrum given below:

$^1$H-NMR (500 MHz, DMSO-D$_6$, ppm): 5.0 (s, 1H, CH), 3.2-4.2 (br, 4H, OH, COOH), 2.9 (s, 2H, —CH$_2$COOH), 2.2-2.3 (m, 2H, —CH$_2$COOC—), 1.1-1.6 (m, 1OH, —(CH$_2$)$_5$—), 0.8-0.9 (t, 3H, CH$_3$—)

(3) Synthesis of hydroxycitric acid-2-octanoate sodium salt

Synthesis was made in a similar manner as in Example 1 (4), except that 10 g of hydroxycitric acid-2-palmitate was replaced with 7.5 g of hydroxycitric acid-2-octanoate synthesized as described in (2) above. Thus, 9.6 g of the objective compound resulted (99% yield).

Example 6

Synthesis of hydroxycitric acid-2-behenate sodium salt (1) Synthesis of hydroxycitric acid tribenzyl ester-2-behenate Synthesis was made in a similar manner as in Example 1 (2), using 479 mg (1.00 mmol) of hydroxycitric acid tribenzyl ester synthesized in a similar manner as in Example 1 (1), 5 ml of THF, 718 mg (2.00 mmol) of behenoyl chloride and 203 mg (2.00 mmol) of triethylamine. Thus, 320 mg of the objective compound was obtained as a white solid (40% yield).

(2) Synthesis of hydroxycitric acid-2-behenate

A 50-ml evaporation flask was charged with 240 mg (0.30 mmol) of hydroxycitric acid tribenzyl ester-2-behenate synthesized in (1) above, 5 ml of THF and 5 ml of ethanol, and synthesis was made in a similar manner as in Example 1 (3). Thus, 140 mg of the objective compound was obtained as a white solid (88% yield).

The structure of the compound obtained was identified by the $^1$H-NMR spectrum given below:

$^1$H-NMR (500 MHz, DMSO-D$_6$+CDCl$_3$, ppm): 5.0 (s, 1H, CH), 3.2-4.2 (br, 4H, OH, COOH), 2.9 (s, 2H, —CH$_2$COOH), 2.2-2.3 (m, 2H, —CH$_2$COOC—), 1.1-1.7 (m, 38H, —(CH$_2$)$_{19}$—), 0.8-0.9 (t, 3H, CH$_3$—)

(3) Synthesis of hydroxycitric acid-2-behenate sodium salt

Synthesis was made in a similar manner as in Example 1 (4), except that 10 g of hydroxycitric acid-2-palmitate was replaced with 11.3 g of hydroxycitric acid-2-behenate synthesized as described in (2) above, and that distilled water was used in an amount of 400 ml. Thus, 13.3 g of the objective compound resulted (99% yield).

Example 7

Synthesis of hydroxycitric acid monomethyl ester-2-palmitate sodium salt (1) Synthesis of hydroxycitric acid dibenzyl ester monomethyl ester-2-palmitate A 100-ml evaporation flask was charged with 996 mg (2.08 mmol) of hydroxycitric acid tribenzyl ester synthesized in Example 1 (1) and 518 mg (2.08 mmol) of dibutyltin oxide, to which 10 ml of methanol was added, followed by stirring under reflux for 70 minutes. The solvent was vacuum evaporated. The residue was combined with 10 ml of dioxane, 632 mg (2.30 mmol) of palmitoyl chloride and 232 mg (2.30 mmol) of triethylamine, followed by stirring at room temperature for 4 hours.

To the reaction liquid, 150 ml and 50 ml of ethyl acetate and water, respectively, were added. The organic phase was washed in the usual way and was dried over anhydrous sodium sulfate. The solvent was evaporated in vacuo, and the residue was subjected to silica gel column chromatography. Elution using a 10:1 mixture of hexane and ethyl acetate gave 920 mg of the objective compound as a white solid (69% yield).

(2) Synthesis of hydroxycitric acid monomethyl ester-2-palmitate

A 50-ml evaporation flask was charged with 321 mg (0.50 mmol) of hydroxycitric acid dibenzyl ester monomethyl ester-2-palmitate synthesized in (1) above, 5 ml of ethanol and 5 ml of DMF.

Subsequently, 40 mg of 10% by mass-palladium activated carbon was added as a catalyst, and catalytic reduction was carried out for 2 hours. The catalyst was filtered off, and the solvent was evaporated in vacuo. To the residue, hexane was added. The solid precipitated was filtered to give 207 mg of the objective compound as a white solid (90% yield).

The structure of the compound obtained was identified by the $^1$H-NMR spectrum given below:

$^1$H-NMR (270 MHz, DMSO-D$_6$, ppm): 5.0 (s, 1H, CH), 3.6 (s, 3H, —COOCH$_3$), 3.2-3.6 (br, 3H, OH, COOH), 2.8-3.0 (m, 2H, —CH$_2$COOH), 2.0-2.2 (m, 2H, —CH$_2$COOC—), 1.1-1.6 (m, 26H, —(CH$_2$)$_{13}$—), 0.8-0.9 (t, 3H, CH$_3$—)

(3) Synthesis of hydroxycitric acid monomethyl ester-2-palmitate sodium salt

Synthesis was made in a similar manner as in Example 1 (4), except that 10 g of hydroxycitric acid-2-palmitate was replaced with 15.5 g of hydroxycitric acid monomethyl ester-2-palmitate synthesized as described in (2) above, and that distilled water was used in an amount of 400 ml. Thus, 17.5 g of the objective compound resulted (99% yield).

Test Example 1

Skin Permeation Test

Tested were:
(a) Hydroxycitric acid calcium salt (SIGMA-ALDRICH JAPAN K.K.), and
(b) Hydroxycitric acid-2-palmitate sodium salt (Example 1)

The above test articles, each 0.5% by mass, were dissolved separately in Dulbecco's PBS (−).

2-cm square skin pieces of minipig (Charles River Laboratories Inc. (United States of America)) were placed in the Netwell (manufactured by Corning Incorporated), and assay rings (Teflon® rings with a center opening) on which a silicon sealant had been applied were pressed and fixed to the epidermis of the skin. Subsequently, 2 ml of a skin culture medium (TOYOBO CO., LTD.) was added to a multiwell plate, and the Netwell was set such that skin lower portions would be soaked. Each of the test article solutions, 0.1 ml, was slowly poured into the opening of assay ring; when no leakage was confirmed, the units were sealed with multiplate seals and were allowed to stand in an incubator at 37° C. and 5% carbon dioxide.

After 4 hours, the test article solutions on the skin pieces were pipetted. The skin pieces were recovered from the Netwell, and distilled water in a washing bottle was poured thereover for washing. The assay rings were detached, and the central portions that had contacted with the solution were punched out with an 8 mm biopsy punch. The excised skin pieces were transferred to 1.5 ml tubes, and 1 ml of 0.5% trypsin solution was added to each tube. The trypsin solution was caused to permeate the skin piece for a day and a night at 4° C.

Next day, the trypsin solution was removed, and the skin pieces were washed three times each with 1 ml of distilled water and were heated in an incubator at 37° C. for 5 minutes, resulting in release of the epidermis. The epidermis that had been released and been floating was peeled with tweezers to separate the skin piece into the epidermis and the dermis. The epidermis and dermis were separately transferred to new 1.5 ml tubes and were heated in an incubator at 37° C. for 30 minutes.

Thereafter, the epidermis and the dermis were fed with 0.1 ml and 0.5 ml of distilled water, respectively, followed by freezing and thawing. They were crushed with a micro-homogenizer designed for 1.5 ml tubes and were centrifuged at 12,000 rpm for 5 minutes to separate uncrushed residues. Thus, a tissue extract was obtained.

The test article in the extract was determined by LC/MS, and the protein in the extract was determined by the Lowry method.

The Lowry method involved the following reagents that had been prepared with reference to Shin Seikagaku Jikken Kouza 1, Protein 1, pp. 85-107.

Reagent 1: 0.1 M sodium hydroxide solution containing 2 wt % sodium carbonate

Reagent 2: 1 wt % sodium citrate solution containing 0.5 wt % copper sulfate pentahydrate Reagent 3: 1 N phenol reagent Reagent 4: 50:1 mixture of Reagent 1 and Reagent 2

Standard sample: albumin solution of 0.1-1.5 mg

The determination procedures were as follows:

400 µl of the reagent 4 was added to a sample tube containing 20 µl of the sample solution or the standard sample solution, followed by mixing. The mixture was allowed to stand at room temperature for at least 15 minutes. Thereafter, 40 µl of the reagent 3 was added and mixed together, and the mixture was allowed to stand at room temperature for at least 30 minutes. The absorbance at 750 nm was measured with a spectrophotometer, and the protein concentration in the sample solution was determined using a calibration curve obtained with the standard sample.

Table 1 shows the amounts of hydroxycitric acid and hydroxycitric acid-2-palmitate in the samples analyzed (nmol/mg skin protein).

TABLE 1

| Sample analyzed (Test article) | Substance to be determined | Determined value |
|---|---|---|
| Epidermis 1 (a) | Hydroxycitric acid | 0.4 |
| Epidermis 2 (b) | Hydroxycitric acid-2-palmitate | 3.4 |
| Dermis 1 (a) | Hydroxycitric acid | 0.2 |
| Dermis 2 (b) | Hydroxycitric acid-2-palmitate | 3.8 |

Table 1 establishes that the sodium salt of acylated hydroxycitric acid derivative (b) can permeate the skin deeper into the dermis layer than hydroxycitric acid calcium salt (a)

Test Example 2

Triglyceride Accumulation Test (1)

Tested were:
(a) Hydroxycitric acid calcium salt,
(b) Hydroxycitric acid-2-palmitate sodium salt (Example 1), and
(c) Hydroxycitric acid monomethyl ester-2-palmitate sodium salt (Example 7)

Mouse 3T3-F442A cells (available from DAINIPPON PHARMACEUTICAL CO., LTD.) were disseminated on a 96-well microplate and were incubated at 37° C. and 5% $CO_2$ over a period of 2 weeks using a DMEM culture medium (available from Invitrogen) containing 10% by mass of FCS.

After differentiation of most cells into adipocytes had been observed with a microscope, the culture medium was replaced with one that contained 100 µM of any one of the test articles (a) to (c). The incubation was continued for another 4 days. The control was incubated using a culture medium that contained no test articles.

After 4 days of incubation, the cells were washed three times with Dulbecco's PBS (−). The triglyceride accumulated in the cells was determined by oil red staining.

Table 2 shows the accumulated triglyceride amounts provided by the test articles relative to the control (100%).

TABLE 2

| | Accumulated triglyceride amount (% relative to control) |
|---|---|
| Control | 100 |
| Test article (a) | 98 |
| Test article (b) | 52 |
| Test article (c) | 84 |

As apparently shown in Table 2, the administration of the test articles can achieve less amounts of accumulated triglyceride than by the administration of the control. Particularly, the sodium salts of acylated hydroxycitric acid derivatives (b) and (c) can provide reduced amounts of accumulated triglyceride than does hydroxycitric acid calcium salt (a). These results establish that the test articles can inhibit synthesis and accumulation of fat.

Test Example 3

Triglyceride Accumulation Test (2)

Tested were:
(a) Hydroxycitric acid calcium salt, and
(b) Hydroxycitric acid-2-palmitate sodium salt (Example 1)

Human white preadipocytes (available from Zen-Bio Inc.) were disseminated on a 96-well microplate and were incubated at 37° C. and 5% $CO_2$ using a white preadipocyte culture medium (PM-1, available from Zen-Bio Inc.). After several days, microscopic observation confirmed that the cells had been confluent, and the medium was replaced with a human white preadipocyte differentiation medium (DM-1, available from Zen-Bio Inc.). After three days, the differentiation medium was changed to a white adipocyte medium (AM-1, available from Zen-Bio Inc.). Incubation was continued while renewing half of the white adipocyte medium every three days.

After differentiation of most cells into adipocytes had been observed with a microscope, the culture medium was replaced with one that contained 100 μM or 1 mM of the test article (a), or 10 μM, 25 μM or 50 μM of the test article (b). The incubation was continued for another 4 days. The control was incubated using a culture medium that contained no test articles.

After 4 days of incubation, the cells were washed three times with Dulbecco's PBS (−). The triglyceride accumulated in the cells was determined by oil red staining. The cell survival rate was measured by a calorimetric method (570 nm) using alamar blue reagent (manufactured by Molecular Probe).

Table 3 shows the accumulated triglyceride amounts and cell survival rates provided by the test articles relative to the control (100%).

TABLE 3

| Article added (tested) | Amount | Accumulated triglyceride amount (% relative to control): 1 | Cell survival rate (% relative to control): 2 | (1/2) × 100 |
|---|---|---|---|---|
| Control | — | 100 | 100 | 100 |
| (a) | 100 μM | 86 | 88 | 98 |
|  | 1 mM | 80 | 94 | 85 |
| (b) | 10 μM | 78 | 100 | 78 |
|  | 25 μM | 72 | 101 | 71 |
|  | 50 μM | 65 | 98 | 66 |

As apparently shown in Table 3, the administration of the test articles can achieve less amounts of accumulated triglyceride than by the administration of the control. Particularly, the sodium salt of acylated hydroxycitric acid derivative (b) can provide reduced amounts of accumulated triglyceride than does hydroxycitric acid calcium salt (a). These results establish that the test articles can inhibit synthesis and accumulation of fat.

Test Example 4

Triglyceride Accumulation Test (3)

Tested were:

(a) Hydroxycitric acid calcium salt, (b) Hydroxycitric acid-2-palmitate sodium salt (Example 1), (d) Hydroxycitric acid-2-octanoate sodium salt (Example 5)

(e) Hydroxycitric acid-2-caprate sodium salt (Example 4), (f) Hydroxycitric acid-2-laurate sodium salt (Example 3), (g) Hydroxycitric acid-2-myristate sodium salt (Example 2), and (h) Hydroxycitric acid-2-behenate sodium salt (Example 6)

Likewise in Test Example 2, mouse 3T3-F442A cells (available from DAINIPPON PHARMACEUTICAL CO., LTD.) were disseminated on a 96-well microplate and were incubated at 37° C. and 5% $CO_2$ over a period of 2 weeks using a DMEM culture medium (available from Invitrogen) containing 10% by mass of FCS.

After differentiation of most cells into adipocytes had been observed with a microscope, the culture medium was replaced with one that contained any one of the test articles (a), (b) and (d) to (h) in an amount of 40 μM, 50 μM, 100 μM, 150 μM, 200 μM, 300 μM, 400 μM, 500 μM or 1000 mM. The incubation was continued for another 4 days. The control was incubated using a culture medium that contained no test articles.

After 4 days of incubation, the cells were washed three times with Dulbecco's PBS (−). The triglyceride accumulated in the cells, and the cell survival rate were measured in similar manners as in Test Example 3.

Table 4 shows lowest concentrations at which the ratio of the accumulated triglyceride amount to the cell survival rate provided by the test articles becomes not more than 80 relative to the control (100).

TABLE 4

| Article added (tested) | Concentration for 20% reduction of TG amount relative to control |
|---|---|
| Control | — |
| (a) | 1000 mM |
| (b) | 50 μM |
| (d) | 200 μM |
| (e) | 200 μM |
| (f) | 150 μM |
| (g) | 100 μM |
| (h) | 40 μM |

Table 4 establishes that it is more effective to add the acylated hydroxycitric acid derivatives in higher concentrations as the chain length thereof is shorter.

Test Example 5

Test (1) of Use in Combination with Caffeine and the Like

Tested were:

(b) Hydroxycitric acid-2-palmitate sodium salt (Example 1), and (i) Caffeine monohydrate (manufactured by Wako Pure Chemical Industries, Ltd.)

Mouse 3T3-F442A cells were incubated in a similar manner as in Test Example 2. After differentiation into adipocytes had been observed, the culture medium was replaced with one that contained 0.05 mM and 0.1 mM of the test article (b) and the test article (i), respectively. The incubation was continued for another 4 days. The control was incubated using a culture medium that contained 0.05 mM of the test article (b).

After 4 days of incubation, the triglyceride accumulated in the cells was determined in a similar manner as in Test Example 2.

Table 5 shows the accumulated triglyceride amount provided by the test articles relative to the control (100%).

TABLE 5

| Article added (tested) | Accumulated triglyceride amount (% relative to control) |
|---|---|
| Control (b) | 100 |
| (b) + (i) | 54 |

Table 5 establishes that the administration of the sodium salt of hydroxycitric acid derivative together with a known lipolytic agent can produce synergistic effects on adipocytes to inhibit the synthesis and accumulation of fat more effectively than does the administration of the control alone.

Test Example 6

Test (2) of Use in Combination with Caffeine and the Like

Tested were:
(b) Hydroxycitric acid-2-palmitate sodium salt (Example 1),
(i) Caffeine monohydrate (manufactured by Wako Pure Chemical Industries, Ltd.), and
(j) L-carnitine hydrochloride (manufactured by SIGMA-ALDRICH JAPAN K.K.)

Human white preadipocytes (available from Zen-Bio Inc.) were incubated in a similar manner as in Test Example 3. After differentiation into adipocytes had been observed, the culture medium was replaced with one that contained 50 μM of (b), or 100 μM of (i), or 50 μM of (j), or 50 μM and 100 μM of (b) and (i) respectively, or 50 μM and 50 μM of (b) and (j) respectively. The incubation was continued for another 4 days. The control was incubated using a culture medium that contained no test articles.

After 4 days of incubation, the triglyceride amount accumulated in the cells, and the cell survival rate were measured in similar manners as in Test Example 5.

Table 6 shows the accumulated triglyceride amounts and cell survival rates provided by the test articles relative to the control (100%).

TABLE 6

| Article added (tested) | Accumulated triglyceride amount (% relative to control): 1 | Cell survival rate (% relative to control): 2 | (1/2) × 100 |
|---|---|---|---|
| Control | 100 | 100 | 100 |
| b | 75 | 100 | 75 |
| i | 86 | 100 | 78 |
| j | 93 | 102 | 91 |
| b + i | 57 | 91 | 63 |
| b + j | 68 | 100 | 68 |

Table 6 establishes that the administration of the sodium salt of hydroxycitric acid derivative together with a known lipolytic agent can produce synergistic effects on adipocytes to inhibit the synthesis and accumulation of fat more effectively than does the administration of the control alone.

Test Example 7

Test for Confirmation of Breakdown of Hydroxycitric Acid Derivative

Tested were:
(a) Hydroxycitric acid calcium salt, and
(b) Hydroxycitric acid-2-palmitate sodium salt (Example 1)

Human white preadipocytes (available from Zen-Bio Inc.) were disseminated in two T-25 flasks and were incubated at 37° C. and 5% $CO_2$ using a white preadipocyte culture medium (PM-1, available from Zen-Bio Inc.). After several days, microscopic observation confirmed that the cells had been confluent, and the medium was replaced with a human white preadipocyte differentiation medium (DM-1, available from Zen-Bio Inc.). After three days, the differentiation medium was changed to a white adipocyte medium (AM-1, available from Zen-Bio Inc.). Incubation was continued while renewing half of the white adipocyte medium every three days.

After differentiation into adipocytes had been observed, the culture media in the flasks were each replaced with one that contained 1 mM of the test article (a) or 0.05 mM of the test article (b). The incubation was continued for another 5 days.

After 5 days of incubation, the cells were released from the flask bottom by adding trypsin and were collected by centrifugation (at 1,000 rpm for 5 minutes). The cells collected were washed two times with Dulbecco's PBS (−), and were transferred to 1.5 ml tubes, followed by freezing and thawing. After addition of 0.15 ml of distilled water, the cells were crushed with a microhomogenizer designed for 1.5 ml tubes and were centrifuged at 12,000 rpm for 5 minutes to remove uncrushed residues. Thus, cell extracts were obtained.

The test article in the extract was determined by LC/MS, and the protein in the extract was determined by the Lowry method as described in Test Example 1.

Table 7 shows the amounts of hydroxycitric acid and hydroxycitric acid-2-palmitate in the samples analyzed (nmol/mg skin protein).

TABLE 7

| Test article | Substance to be determined | Determined value |
|---|---|---|
| (a) | Hydroxycitric acid | 0.6 |
| (b) | Hydroxycitric acid | 3.0 |
|  | Hydroxycitric acid-2-palmitate | 4.7 |

Table 7 establishes that hydroxycitric acid-2-palmitate is broken down within adipocytes to generate hydroxycitric acid, and that the sodium salt of acylated hydroxycitric acid derivative (b) can provide higher hydroxycitric acid concentration in adipocytes than does hydroxycitric acid calcium salt (a).

In Examples 8 to 15 presented below, the amounts are indicated in % by mass to the total (100) of the ingredients unless otherwise mentioned. Hydroxycitric acid-2-palmitate sodium salt used herein was synthesized in a similar manner as in Example 1.

Example 8

Skin toners were manufactured according to the following formulations.

Formulation Example 1

| A. | |
|---|---|
| Dipotassium glycyrrhizinate | 0.2% |
| Hydroxycitric acid-2-palmitate sodium salt | 1.0% |
| Citric acid | 0.1% |
| Sodium citrate | 0.3% |
| Purified water | Balance |
| B. | |
| Polyoxyethylene sorbitol tetraoleate | 0.9% |
| Sorbitan monooleate | 0.1% |
| Olive oil | 0.1% |
| Dipropylene glycol | 5.0% |

-continued

| | |
|---|---|
| Methylparaben | 0.1% |
| Ethanol | 10.0% |

Formulation Example 2

| A. | |
|---|---|
| Sodium citrate | 0.1% |
| Glycerin | 8.0% |
| Sodium pyrrolidonecarboxylate | 1.0% |
| Trehalose | 0.03% |
| 1,3-butylene glycol | 5.0% |
| Hydroxycitric acid-2-palmitate sodium salt | 1.0% |
| Purified water | Balance |
| B. | |
| Polyoxyethylene polyoxypropylene decyltetradecyl ether | 0.6% |
| Methylparaben | 0.1% |
| Ethanol | 10.0% |

Formulation Example 3

| A. | |
|---|---|
| Polyvinyl alcohol | 0.1% |
| Carboxyvinyl polymer | 0.2% |
| Glycerin | 3.0% |
| Trisodium edetate | 0.1% |
| Sodium hydroxide | 0.05% |
| 2-amino-2-methyl-1-propanol | 0.06% |
| Hydroxycitric acid-2-palmitate sodium salt | 1.0% |
| Caffeine | 0.1% |
| Purified water | Balance |
| B. | |
| Ethanol | 20.0% |
| Polyoxyethylene oleyl ether | 0.3% |
| Methylparaben | 0.1% |
| Menthol | 0.1% |

In Formulation Examples above, the ingredients of A and B were mixed together separately and were heated at 50° C. to give solutions. Subsequently, with A being stirred, small portions of B was added to A and was dissolved therein. The resultant solution was cooled with stirring. When the temperature reached 30° C., the stirring was cancelled and the solution was allowed to stand. Formulation Example 1 produced a normal-type skin toner, Formulation Example 2 a high moisture retention type, and Formulation Example 3 a firming type.

Formulation Example 4

| A. | |
|---|---|
| 1,3-butylene glycol | 5.02% |
| Di(cholesteryl/behenyl/octyldodecyl)lauroyl glutamate | 0.5% |
| Trehalose | 0.03% |
| Trioctanoin | 0.03% |

-continued

| | |
|---|---|
| PEG-58 hydrogenated castor oil isostearate | 1.5% |
| PEG-60 hydrogenated castor oil | 0.5% |
| Methylparaben | 0.2% |
| Propylparaben | 0.01% |
| Tocopherol | 0.05% |
| B. | |
| Hydroxycitric acid-2-palmitate sodium salt | 1.0% |
| Sodium malate | 0.1% |
| Malic acid | Moderate amount |
| Purified water | Balance |

The ingredients of A and B were mixed together separately and were heated at 60° C. to give solutions. Subsequently, with A being stirred, B was admixed with A and the mixture was cooled to form a uniform solution. Formulation Example 4 thus produced an alcohol-free hypoallergenic skin toner.

Example 9

Skin milks were manufactured according to the following formulations.

Formulation Example 5

| A. | |
|---|---|
| Squalane | 10.0% |
| Polyoxyethylene glyceryl isostearate | 3.5% |
| Polyoxyethylene Hydrogenated castor oil triisostearate | 6.5% |
| Polyoxyethylene Hydrogenated castor oil pyroglutamate isostearate | 12.0% |
| Methylparaben | 0.1% |
| B. | |
| Hydroxycitric acid-2-palmitate sodium salt | 2.0% |
| Purified water | Balance |

The ingredients of A and B were mixed together separately, and A and B were heated at 70° C. and 50° C., respectively, to give solutions. Subsequently, with A being stirred, small portions of B was added to A to form an emulsion. Cooling with stirring formed a milky liquid at near 30° C. The milky liquid composition was diluted ten times with purified water and was cooled to room temperature to yield a skin milk.

Formulation Example 6

| A. | |
|---|---|
| Liquid paraffin | 10.6% |
| Isopropyl myristate | 0.6% |
| Oleyl alcohol | 1.2% |
| Polyoxyethylene stearyl ether | 3.4% |
| PEG distearate | 1.9% |
| Polyoxyethylene polyoxypropylene tetradecyl ether | 0.4% |
| B. | |
| Sodium stearoylglutamate | 0.1% |
| Propylene glycol | 1.4% |
| Methylparaben | 0.1% |
| PEG-400 | 0.2% |
| Hydroxycitric acid-2-palmitate sodium salt | 2.0% |
| Purified water | Balance |

The ingredients of A and B were mixed together separately, and A and B were heated at 70° C. and 75° C., respectively, to give solutions. Subsequently, with B being stirred, small portions of A was added to B to form an emulsion. Cooling with stirring formed a milky liquid at near 40° C. The milky liquid composition was cooled to room temperature to yield a skin milk.

Formulation Example 7

| A. | |
|---|---|
| Polyoxyethylene sorbitan monostearate | 1.0% |
| Polyoxyethylene sorbitol tetraoleate | 0.5% |
| Sorbitan monostearate | 1.0% |
| Stearic acid | 0.5% |
| Behenyl alcohol | 0.5% |
| Beeswax | 0.5% |
| Squalane | 10.0% |
| Glyceryl tri-2-ethylhexanoate | 10.0% |
| Decaglyceryl decaoleate | 3.0% |
| 1,3-butylene glycol | 7.0% |
| Methylparaben | 0.1% |
| B. | |
| Xanthan gum | 0.04% |
| Carboxyvinyl polymer | 0.08% |
| Hydroxycitric acid-2-palmitate sodium salt | 2.0% |
| Purified water | Balance |
| C. | |
| Triethanol amine | 0.05% |
| Purified water | 4.95% |

The ingredients of A, B and C were mixed together separately, and A and B were heated at 80° C. to give solutions whilst C was homogenized at room temperature. Subsequently, with A being stirred, B was added to A to form an emulsion, to which C was then added. Cooling with stirring formed a milky liquid at near 40° C. The milky liquid composition was cooled to room temperature to yield a skin milk.

Example 10

Semitransparent gels were manufactured according to the following formulations.

Formulation Example 8

| A. | |
|---|---|
| Agar | 2.0% |
| Xanthan gum | 0.2% |
| Caffeine | 0.1% |
| Purified water | 50.0% |
| B. | |
| Glycerin | 7.0% |
| PEG-1500 | 8.0% |
| Methylparaben | 0.1% |
| Hydroxycitric acid-2-palmitate sodium salt | 2.0% |
| Purified water | Balance |

The ingredients of A and B were mixed together separately, and A and B were heated at 90° C. and 50° C., respectively, to give dispersions. Subsequently, A was cooled to 50° C. With A being stirred, B was added to A and the mixture was gelled by cooling to not more than 30° C. with stirring. When the gel became sufficiently solid, it was crushed into a microgel with use of a dispersing device, followed by deaeration to produce a uniform (semitransparent) gel.

Formulation Example 9

| A. | |
|---|---|
| Carboxyvinyl polymer | 0.35% |
| Purified water | 50.0% |
| B. | |
| Sodium hydroxide | 0.1% |
| Purified water | 10.0% |
| C. | |
| Sodium hyaluronate (1% aqueous solution) | 6.0% |
| Hydroxycitric acid-2-palmitate sodium salt | 2.0% |
| Purified water | Balance |
| D. | |
| Polyoxyethylene polyoxypropylene tetradecyl ether | 0.3% |
| Ethanol | 5.0% |
| Methylparaben | 0.1% |
| E. | |
| Perfluoropolyether | 0.2% |

The ingredients of A, B, C and D were mixed together separately. A and B were allowed to form solutions at room temperature, and C and D were heated at 50° C. and 40° C., respectively, to give solutions. Subsequently, with A being stirred, B was added to A and the mixture was gelled. Thereafter, C, D and E were added to the gel and mixed together by stirring, followed by deaeration to produce a uniform (semitransparent) gel.

Formulation Example 10

| A. | |
|---|---|
| Carboxyvinyl polymer | 0.5% |
| Purified water | 40.0% |
| B. | |
| Potassium hydroxide | 0.1% |
| Purified water | 10.0% |
| C. | |
| Dipropylene glycol | 10.0% |
| Methylparaben | 0.1% |
| Dipotassium glycyrrhizinate | 0.05% |
| Hydrolyzed collagen | 0.05% |
| Hydroxycitric acid-2-palmitate sodium salt | 2.0% |
| Purified water | Balance |

The ingredients of A, B and C were mixed together separately. A and B were allowed to form solutions at room temperature, and C was heated at 50° C. to give a solution. Subsequently, with A being stirred, B was added to A and the mixture was gelled. Thereafter, C was added to the gel and mixed together by stirring, followed by deaeration to produce a uniform (semitransparent) gel.

Formulation Example 11

| A. | |
|---|---|
| Glycerin | 10.0% |
| 1,3-butylene glycol | 6.0% |
| Dimethicone | 2.0% |
| PEG-60 hydrogenated castor oil | 0.6% |
| Laureth-2 | 0.1% |
| Laureth-21 | 0.1% |
| Methylparaben | 0.26% |
| Propylparaben | 0.1% |
| Ethylparaben | 0.1% |
| Phenoxyethanol | 0.1% |
| Tocopherol acetate | 0.1% |
| Chitosan succinamide | 0.01% |
| Yeast extract | 0.1% |
| Ethanol | 0.01% |
| Perfume | 0.01% |

| B. | |
|---|---|
| Hydroxycitric acid-2-palmitate sodium salt | 1.0% |
| Carboxyvinyl polymer | 0.5% |
| Urea | 0.02% |
| Glucosamine hydrochloride | 0.01% |
| Disodium edetate | 0.01% |
| Purified water | 50.0% |

| C. | |
|---|---|
| Arginine | 0.63% |
| Purified water | Balance |

The ingredients of A, B and C were mixed together separately. A was heated at 60° C. to give a solution, and B and C were allowed to form solutions at room temperature. Subsequently, with A being stirred, B was added to A and the mixture was gelled. Thereafter, C was added to the gel and mixed together by stirring, followed by cooling to room temperature to produce a uniform (semitransparent) gel.

Formulation Example 12

| A. | |
|---|---|
| Glycerin | 50.0% |
| Hydroxycitric acid-2-palmitate sodium salt | 1.0% |
| Tourmaline | 5.0% |
| Olive oil | 1.0% |
| PEG-12 | 28.0% |
| PEG-75 | 7.5% |
| Polyglyceryl laurate | 1.0% |
| Ethanol | 0.49% |
| (Acrylic acid/alkyl (C10-30) acrylate) copolymer | 0.11% |
| Methylparaben | 0.1% |
| Propylparaben | Moderate amount |
| *Ginkgo* extract | Moderate amount |
| Tea extract | Moderate amount |
| Horse chestnut extract | Moderate amount |
| Brown algae extract | Moderate amount |

| B. | |
|---|---|
| Carboxyvinyl polymer | 0.07% |
| Purified water | 3.0% |

| C. | |
|---|---|
| Sodium hydroxide | 0.01% |
| Purified water | Balance |

The ingredients of A, B and C were mixed together separately. A was heated at 60° C. to give a solution, and B and C were allowed to form solutions at room temperature. Subsequently, with A being stirred, B was added to A and the mixture was gelled. Thereafter, C was added to the gel and mixed together by stirring, followed by cooling to room temperature to produce a uniform (semitransparent) gel.

Formulation Example 13

| A. | |
|---|---|
| Decamethylcyclopentasiloxane | 20.0% |
| Potassium ascorbate | 3.0% |
| Hydroxycitric acid-2-palmitate sodium salt | 1.0% |

| B. | |
|---|---|
| Squalane | 50.0% |
| Light liquid isoparaffin | Balance |
| Dextrin palmitate | 8.0% |

| C. | |
|---|---|
| Octyl paramethoxycinnamate | 1.0% |
| Phenoxyethanol | 0.5% |
| α-tocopherol | 0.1% |

The ingredients of A, B and C were separately weighed out. The ingredients of A were kneaded at room temperature with a bead mill. The ingredients of B were heated to give a uniform solution. The ingredients of C were allowed to form a solution at room temperature. Subsequently, with B being stirred, C was added to B. The mixture was homogenized and was cooled to room temperature with stirring. Thereafter, A was added and the mixture was stirred sufficiently to produce a uniform (semitransparent) gel.

Example 11

Serums were manufactured according to the following formulations.

Formulation Example 14

| A. | |
|---|---|
| Xanthan gum | 0.4% |
| Hydroxyethyl cellulose | 0.1% |
| Carboxyvinyl polymer | 0.1% |
| 1,3-butylene glycol | 5.0% |
| Purified water | 50.0% |

| B. | |
|---|---|
| Potassium hydroxide (1% aqueous solution) | 2.5% |
| Purified water | 10.0% |

| C. | |
|---|---|
| Hydroxycitric acid-2-palmitate sodium salt | 2.0% |
| Caffeine | 1.0% |
| Purified water | Balance |

| D. | |
|---|---|
| Methylparaben | 0.1% |
| Ethanol | 3.0% |

The ingredients of A, B, C and D were mixed together separately. A, B and D were allowed to form solutions at room temperature, and C was heated at 50° C. to give a solution.

Subsequently, with A being stirred, B was added to A to form a viscous liquid. Thereafter, C and D were added thereto and mixed together by stirring to produce a uniform liquid (serum).

Formulation Example 15

| A. | |
|---|---|
| 1,3-butylene glycol | 10.0% |
| Glycerin | 5.0% |
| Sodium hyaluronate | 0.2% |
| Xanthan gum | 0.2% |
| Dipotassium glycyrrhizinate | 0.02% |
| Hydroxycitric acid-2-palmitate sodium salt | 1.0% |
| Purified water | Balance |
| B. | |
| Ethanol | 3.0% |
| Hydrogenated lecithin | 0.5% |
| Trioctanoin | 0.3% |
| Diphenyl dimethicone | 0.2% |
| Methylparaben | 0.22% |
| Phenoxyethanol | 0.08% |
| PEG-50 hydrogenated castor oil | 0.1% |
| PEG-60 hydrogenated castor oil | 0.1% |
| α-tocopherol | 0.01% |
| Polyglyceryl-10 myristate | 0.05% |

The ingredients of A and B were mixed together separately, and A and B were heated at 50° C. to give solutions. Subsequently, with A being stirred, B was admixed with A with stirring, and the mixture was cooled with stirring to produce a uniform liquid (serum).

Formulation Example 16

| A. | |
|---|---|
| Xanthan gum | 0.4% |
| Hydroxyethyl cellulose | 0.4% |
| 1,3-butylene glycol | 3.0% |
| Glycerin | 3.0% |
| Methylparaben | 0.1% |
| Purified water | Balance |
| B. | |
| Hydroxycitric acid-2-palmitate sodium salt | 5.0% |
| 1,2-hexanediol | 4.0% |
| Purified water | 50.0% |
| C. | |
| Magnesium ascorbic acid-2-phosphate | 1.5% |
| Sodium ascorbic acid-2-phosphate | 1.5% |
| Sodium citrate | 0.5% |
| Tetrasodium edetate | 0.1% |
| Purified water | 9.4% |

The ingredients of A, B and C were mixed together separately. A and C were allowed to form solutions at room temperature, and B was heated at 50° C. to give a solution. Subsequently, with A being stirred, B was added to A to form a viscous liquid. Thereafter, C was admixed with stirring to produce a uniform liquid (serum). In this formulation, the amount of 1,2-hexanediol was controlled to permit high-concentration addition of hydroxycitric acid-2-palmitate sodium salt.

Example 12

Cream was manufactured according to the following formulation.

Formulation Example 17

| A. | |
|---|---|
| Hydrogenated rapeseed oil alcohol | 4.2% |
| Isononyl isononanoate | 6.0% |
| Squalane | 9.6% |
| Octyldodecyl myristate | 4.8% |
| Polyglyceryl monostearate | 2.0% |
| Glyceryl stearate | 1.0% |
| Propylparaben | 0.05% |
| Xanthan gum | 0.1% |
| α-tocopherol | 0.5% |
| B. | |
| 1,3-butylene glycol | 4.8% |
| Glycerin | 4.8% |
| Hydroxycitric acid-2-palmitate sodium salt | 1.0% |
| Sodium ascorbic acid-2-phosphoric acid-6-palmitate | 1.0% |
| Methylparaben | 0.1% |
| Purified water | Balance |

The ingredients of A and B were mixed together separately, and A and B were heated at 85° C. to give solutions. Subsequently, with A being stirred, B was added to A to give an emulsion. The emulsion was cooled with stirring. When the temperature approximately reached 40° C., the stirring was cancelled and the emulsion was deaerated to produce a cream.

Example 13

Sheet-like cosmetic packs were manufactured according to the following formulations.

Formulation Example 18

| A. | |
|---|---|
| Glycerin | 30.0% |
| Magnesium hydroxide-Aluminum hydroxide co-precipitate | 1.0% |
| B. | |
| Diisopropanolamine | 1.0% |
| Sodium polyacrylate | 2.0% |
| Acrylic acid/sodium acrylate copolymer (50/50 molar ratio) | 2.0% |
| Hydroxycitric acid-2-palmitate sodium salt | 2.0% |
| Magnesium ascorbic acid-2-phosphate | 3.0% |
| Purified water | Balance |

Formulation Example 19

| A. | |
|---|---|
| 1,3-butylene glycol | 30.0% |
| Aluminum hydroxide gel/sodium hydrogencarbonate coprecipitate | 0.05% |

-continued

B.

| | |
|---|---|
| Sodium acrylate/acrylic acid copolymer (70/30 molar ratio) | 1.0% |
| Polyacrylic acid | 1.0% |
| N-vinylacetamide/sodium acrylate copolymer (9/1 weight ratio) | 3.0% |
| Aluminum lactate | 0.05% |
| 10% aqueous ammonia solution | 0.01% |
| Hydroxycitric acid-2-palmitate sodium salt | 2.0% |
| Magnesium ascorbic acid-2-phosphate | 0.01% |
| Purified water | Balance |

In Formulation Examples above, the ingredients of A and B were mixed together separately; A was allowed to form a dispersion at room temperature and B was heated at 50° C. to give a solution. Subsequently, B was cooled to room temperature with stirring, and A was gradually added to B with kneading. The resultant sol was applied on a polypropylene liner with a knife coater with clearances of 0.5 mm. Thereafter, a nonwoven fabric was attached onto the sol and these were placed in an aluminum laminated bag, which was then heat sealed. After three days of aging, a sheet-like cosmetic pack was obtained.

Example 14

A peel-off pack was manufactured according to the following formulation.

Formulation Example 20

| A. | |
|---|---|
| Polyvinyl alcohol | 13.0% |
| Carrageenan | 0.5% |
| Hydroxycitric acid-2-palmitate sodium salt | 1.0% |
| Purified water | Balance |
| B. | |
| 1,3-butylene glycol | 3.0% |
| Methylparaben | 0.1% |
| Ethanol | 8.0% |

The ingredients of A and B were mixed together separately. A was caused to swell by heating at 50° C. and B was allowed to form a solution at room temperature. Subsequently, with A being stirred, B was gradually added to A and mixed together. Thereafter, the mixture was cooled with stirring. When the temperature approximately reached 30° C., the stirring was cancelled and the mixture was allowed to stand to produce a peel-off pack.

Example 15

Bath agents were manufactured according to the following formulations.

Formulation Example 21

| | |
|---|---|
| Polyoxyethylene sorbitol tetraoleate | 14.0% |
| Polyoxyethylene oleyl ether | 3.0% |
| Sorbitan sesquioleate | 3.0% |
| Squalane | 10.0% |
| Jojoba oil | 20.0% |
| Avocado oil | 5.0% |
| Propylparaben | 0.1% |
| Hydroxycitric acid-2-palmitate sodium salt | 20.0% |
| Liquid paraffin | Balance |

Formulation Example 22

| | |
|---|---|
| Sodium hydrogencarbonate | 35.5% |
| Citric acid | 37.1% |
| Polyethylene glycol | 2.1% |
| Magnesium oxide | 1.1% |
| α-tocopherol | 1.2% |
| Sodium ascorbic acid-2-phosphate | 1.5% |
| Ascorbic acid-2-glucoside | 1.5% |
| Hydroxycitric acid-2-palmitate sodium salt | 20.0% |

In Formulation Examples above, the ingredients were stirred at ordinary temperature to uniformity to produce bath agents.

INDUSTRIAL APPLICABILITY

The hydroxycitric acid derivatives and salts thereof according to the present invention possess slimming effects and are suitable for use as active ingredients in skin external preparations and cosmetics. Therefore, the present invention is useful in the field of production of skin external preparations and cosmetics.

The invention claimed is:

1. A hydroxycitric acid derivative represented by the formula (I) below or salt thereof:

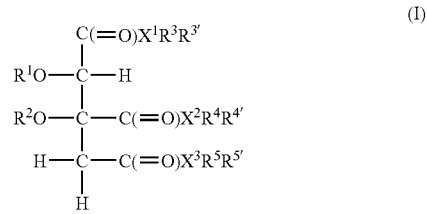

wherein $R^1$ and $R^2$ are each a hydrogen atom or a group removable by biological enzyme reaction (with the proviso that $R^1$ and $R^2$ cannot be hydrogen atoms at the same time), the removable group being selected from those represented by the formula (Ia) below; $X^1$ to $X^3$ are each a nitrogen atom or an oxygen atom; and $R^3$, $R^4$, $R^5$, $R^{3'}$, $R^{4'}$ and $R^{5'}$ are each a hydrogen atom or a chain hydrocarbon group of 1 to 30 carbon atoms that may have a branch or an unsaturated bond (with the proviso that when any of $X^1$, $X^2$ and $X^3$ is an oxygen atom, corresponding $R^{3'}$, $R^{4'}$ or $R^{5'}$ does not exist);

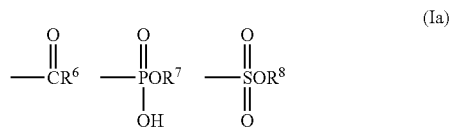

wherein $R^6$ is a hydrogen atom, a phenyl group, a naphthyl group, a furyl group, a thienyl group, a pyridyl group, or a chain hydrocarbon group of 7 to 23 carbon atoms that may have a branch, an unsaturated bond or a substituent group selected from the group consisting of a halogen atom, an amino group, a cyano group, an alkoxy group and a nitro group, and $R^7$ and $R^8$ are each a hydrogen atom, an aryl group, or a chain hydrocarbon group of 1 to 30 carbon atoms that may have a branch, an unsaturated bond or a substituent group selected from the group consisting of a halogen atom, an amino group, a cyano group, an alkoxy group and a nitro group.

2. The hydroxycitric acid derivative or salt thereof according to claim 1, wherein in the formula (Ia), $R^6$ is a chain hydrocarbon group of 7 to 23 carbon atoms that may have a branch, an unsaturated bond or a substituent group selected from the group consisting of a halogen atom, an amino group, a cyano group, an alkoxy group and a nitro group, and $R^7$ and $R^8$ are each a hydrogen atom or a chain hydrocarbon group of 8 to 24 carbon atoms that may have a branch, an unsaturated bond or a substituent group selected from the group consisting of a halogen atom, an amino group, a cyano group, an alkoxy group and a nitro group.

3. The hydroxycitric acid derivative or salt thereof according to claim 1, wherein in the formula (I), $R^3$ to $R^5$ are each a hydrogen atom or a chain hydrocarbon group of 1 to 30 carbon atoms that may have a branch or an unsaturated bond, and $X^1$ to $X^3$ are all oxygen atoms; and wherein in the formula (Ia), $R^6$ is a chain hydrocarbon group of 7 to 23 carbon atoms that may have a branch, an unsaturated bond or a substituent group selected from the group consisting of a halogen atom, an amino group, a cyano group, an alkoxy group and a nitro group, and $R^7$ and $R^8$ are each a hydrogen atom or a chain hydrocarbon group of 8 to 24 carbon atoms that may have a branch, an unsaturated bond or a substituent group selected from the group consisting of a halogen atom, an amino group, a cyano group, an alkoxy group and a nitro group.

4. The hydroxycitric acid derivative or salt thereof according to claim 1, wherein in the formula (I), $R^2$ is a hydrogen atom, $R^3$ to $R^5$ are all hydrogen atoms, and $X^1$ to $X^3$ are all oxygen atoms; and wherein in the formula (Ia), $R^6$ is a chain hydrocarbon group of 13 to 21 carbon atoms that may have a branch, an unsaturated bond or a substituent group selected from the group consisting of a halogen atom, an amino group, a cyano group, an alkoxy group and a nitro group.

5. The hydroxycitric acid derivative or salt thereof according to claim 1, wherein in the formula (I), $R^2$ is a hydrogen atom, $R^3$ to $R^5$ are each a hydrogen atom or a chain hydrocarbon group of 1 to 30 carbon atoms that may have a branch or an unsaturated bond (with the proviso that $R^3$ to $R^5$ cannot be hydrogen atoms at the same time), and $X^1$ to $X^3$ are all oxygen atoms; and wherein in the formula (Ia), $R^6$ is a chain hydrocarbon group of 13 to 21 carbon atoms that may have a branch, an unsaturated bond or a substituent group selected from the group consisting of a halogen atom, an amino group, a cyano group, an alkoxy group and a nitro group.

6. A process for producing the hydroxycitric acid derivative or salt thereof as described in claim 1, which process comprises reacting hydroxycitric acid and/or an alkali metal salt thereof and/or an alkaline earth metal salt thereof, with a carboxylic acid derivative, a phosphoric acid derivative or a sulfonic acid derivative that is capable of in vivo cleavage, in a solvent.

7. A process for producing the hydroxycitric acid derivative or salt thereof as described in claim 4, which process comprises:

a first step comprising reacting hydroxycitric acid and/or an alkali metal salt thereof and/or an alkaline earth metal salt thereof, with an alcohol in a solvent to prepare a hydroxycitric acid (tri)ester;

a second step comprising reacting the compound obtained in the first step with an aliphatic carboxylic acid derivative capable of in vivo cleavage to esterify a hydroxyl group of the compound obtained in the first step; and a third step comprising cleaving ester linkage moieties of the compound obtained in the second step so as to cleave part or all of the ester linkage moieties formed in the first step.

8. A skin external preparation comprising the hydroxycitric acid derivative and/or salt thereof as described in claim 1.

9. The skin external preparation according to claim 8, wherein the preparation contains the hydroxycitric acid derivative and/or salt thereof in an amount of 0.01 to 20% by mass.

10. The skin external preparation according to claim 8, wherein the preparation further contains a substance capable of increasing hormone-sensitive lipase activity.

11. The skin external preparation according to claim 8, wherein the preparation further contains a substance capable of facilitating breakdown of fatty acids.

12. A cosmetic comprising the skin external preparation as described in claim 8.

13. A process for producing the hydroxycitric acid derivative or salt thereof as described in claim 2, which process comprises reacting hydroxycitric acid and/or an alkali metal salt thereof and/or an alkaline earth metal salt thereof, with a carboxylic acid derivative, a phosphoric acid derivative or a sulfonic acid derivative that is capable of in vivo cleavage, in a solvent.

14. A process for producing the hydroxycitric acid derivative or salt thereof as described in claim 3, which process comprises reacting hydroxycitric acid and/or an alkali metal salt thereof and/or an alkaline earth metal salt thereof, with a carboxylic acid derivative, a phosphoric acid derivative or a sulfonic acid derivative that is capable of in vivo cleavage, in a solvent.

15. A process for producing the hydroxycitric acid derivative or salt thereof as described in claim 4, which process comprises reacting hydroxycitric acid and/or an alkali metal salt thereof and/or an alkaline earth metal salt thereof, with a carboxylic acid derivative, a phosphoric acid derivative or a sulfonic acid derivative that is capable of in vivo cleavage, in a solvent.

16. A process for producing the hydroxycitric acid derivative or salt thereof as described in claim 5, which process comprises reacting hydroxycitric acid and/or an alkali metal salt thereof and/or an alkaline earth metal salt thereof, with a carboxylic acid derivative, a phosphoric acid derivative or a sulfonic acid derivative that is capable of in vivo cleavage, in a solvent.

17. A process for producing the hydroxycitric acid derivative or salt thereof as described in claim 5, which process comprises:
- a first step comprising reacting hydroxycitric acid and/or an alkali metal salt thereof and/or an alkaline earth metal salt thereof, with an alcohol in a solvent to prepare a hydroxycitric acid (tri)ester;
- a second step comprising reacting the compound obtained in the first step with an aliphatic carboxylic acid derivative capable of in vivo cleavage to esterify a hydroxyl group of the compound obtained in the first step; and
- a third step comprising cleaving ester linkage moieties of the compound obtained in the second step so as to cleave part or all of the ester linkage moieties formed in the first step.

18. The skin external preparation according to claim 9, wherein the preparation further contains a substance capable of increasing hormone-sensitive lipase activity.

19. The skin external preparation according to claim 9, wherein the preparation further contains a substance capable of facilitating breakdown of fatty acids.

20. A cosmetic comprising the skin external preparation as described in claim 9.

21. A cosmetic comprising the skin external preparation as described in claim 10.

22. A cosmetic comprising the skin external preparation as described in claim 11.

23. A cosmetic comprising the skin external preparation as described in claim 18.

24. A cosmetic comprising the skin external preparation as described in claim 19.

* * * * *